(12) United States Patent
Lawrence, III et al.

(10) Patent No.: US 9,796,089 B2
(45) Date of Patent: Oct. 24, 2017

(54) SUPERVISED AUTONOMOUS ROBOTIC SYSTEM FOR COMPLEX SURFACE INSPECTION AND PROCESSING

(71) Applicant: Carnegie Mellon University, Pittsburgh, PA (US)

(72) Inventors: Stuart Edwin Lawrence, III, Pittsburgh, PA (US); Christopher L Baker, Allison Park, PA (US); Christopher Randolph Baker, New Kensington, PA (US); David G Galati, Pittsburgh, PA (US); Justin C Haines, Pittsburgh, PA (US); Herman Herman, Gibsonia, PA (US); Alonzo J Kelly, Sewickley, PA (US); Eric Meyhofer, Pittsburgh, PA (US); Anthony Stentz, Pittsburgh, PA (US); Jean-Sebastien Valois, Pittsburgh, PA (US); Andrew Strat, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 14/774,731

(22) PCT Filed: Mar. 17, 2014

(86) PCT No.: PCT/US2014/030242
§ 371 (c)(1),
(2) Date: Sep. 11, 2015

(87) PCT Pub. No.: WO2014/145471
PCT Pub. Date: Sep. 18, 2014

(65) Prior Publication Data
US 2016/0016312 A1    Jan. 21, 2016

Related U.S. Application Data

(60) Provisional application No. 61/852,310, filed on Mar. 15, 2013.

(51) Int. Cl.
*G06F 19/00* (2011.01)
*B25J 9/16* (2006.01)
(Continued)

(52) U.S. Cl.
CPC ........ *B25J 9/1671* (2013.01); *B23Q 17/2233* (2013.01); *G01B 11/24* (2013.01);
(Continued)

(58) Field of Classification Search
CPC .. B25J 9/1671; B25J 9/042; B25J 5/02; B24C 3/04; G01B 11/24; G01N 21/9515; Y10S 901/06; Y10S 901/41; Y10S 901/28
See application file for complete search history.

(56) References Cited

U.S. PATENT DOCUMENTS

| 5,281,798 A | 1/1994 | Hamm et al. |
| 5,429,682 A * | 7/1995 | Harlow, Jr. ............. B05B 12/02 |
| | | 118/316 |

(Continued)

FOREIGN PATENT DOCUMENTS

| WO | 91/14539 A1 | 10/1991 |
| WO | 98/51452 A1 | 11/1998 |

OTHER PUBLICATIONS

Byron Spice: "Concurrent Technologies to Develop Robotic Laser System That Strips Paint From Aircraft"—CMU News, Carnegie Mellon University press release, Nov. 26, 2012.

*Primary Examiner* — Nicholas Kiswanto
*Assistant Examiner* — Rachid Bendidi
(74) *Attorney, Agent, or Firm* — Dennis M. Carleton

(57) ABSTRACT

The invention disclosed herein describes a supervised autonomy system designed to precisely model, inspect and process the surfaces of complex three-dimensional objects. The current application context for this system is laser coating removal of aircraft, but this invention is suitable for (Continued)

use in a wide variety of applications that require close, precise positioning and maneuvering of an inspection or processing tool over the entire surface of a physical object. For example, this system, in addition to laser coating removal, could also apply new coatings, perform fine-grained or gross inspection tasks, deliver and/or use manufacturing process tools or instruments, and/or verify the results of other manufacturing processes such as but not limited to welding, riveting, or the placement of various surface markings or fixtures.

33 Claims, 15 Drawing Sheets

(51) Int. Cl.
G01B 11/24 (2006.01)
G01N 21/95 (2006.01)
B23Q 17/22 (2006.01)
G05B 19/4099 (2006.01)

(52) U.S. Cl.
CPC ..... *G01N 21/9515* (2013.01); *G05B 19/4099* (2013.01); *G05B 2219/45071* (2013.01); *Y10S 901/06* (2013.01); *Y10S 901/28* (2013.01); *Y10S 901/41* (2013.01)

(56) References Cited

U.S. PATENT DOCUMENTS

| 6,201,546 | B1 | 3/2001 | Bodor et al. | |
|---|---|---|---|---|
| 8,031,933 | B2 | 10/2011 | Se et al. | |
| 2006/0181700 | A1* | 8/2006 | Andrews | G01N 21/21 356/237.2 |
| 2006/0212150 | A1* | 9/2006 | Sims | G06Q 30/00 700/98 |
| 2011/0087354 | A1* | 4/2011 | Tye | A63H 9/00 700/98 |
| 2011/0218668 | A1 | 9/2011 | Morfino | |

* cited by examiner

SUPERVISED AUTONOMOUS ROBOTIC SYSTEM FOR COMPLEX SURFACE INSPECTION AND PROCESSING

RELATED APPLICATIONS

This application claims the benefit of U.S. Provisional Application No. 61/852,310, filed Mar. 15, 2013.

GOVERNMENT INTEREST

This invention was made partially with government support under the U.S. Air Force number FA5320-09-D-5601 & U.S. Army W91ZLK-10-D-0005 Task 0793. The government has certain rights in this invention.

FIELD OF THE INVENTION

This invention relates to the control of robotic manipulators to move a surface processing device over the surface of a three dimensional object. In particular, the present application has utility for removing paint from the surfaces of aircraft fuselage, wings and control surfaces.

BACKGROUND OF THE INVENTION

Scenarios which require a robot to process, visit, or in some way perform an action over the entirety of a given workspace are known as coverage problems. Common examples of coverage problems include lawn mowing, exploratory mapping, household vacuuming, surveillance, surface painting and de-painting, pesticide spraying, and many others. While these problems have much in common, they also differ in important ways which have considerable impact on the strategies used to optimize and automate their solutions. In the majority of coverage problems, the coverage requirements are discretized into uniformly-sized two- or three-dimensional cells, where each cell represents an area or volume that may require coverage. By using appropriate models, it is possible to estimate which cells will be "covered" by a particular combination of world state, robot state, and robot action. Coverage planners use this estimate along with a hierarchical system of algorithms to determine a sequence of robot actions that efficiently satisfy the coverage requirements while obeying any process-specific constraints.

The nature of these algorithms is strongly influenced by criteria such as the level of environmental uncertainty, environmental and robotic constraints and the nature of the coverage action. Some problems, such as exploratory mapping, operate on a dynamic environment with many unknowns. In these problems, coverage planners must plan adaptively in real time, as the "correct" action changes constantly as new information is discovered. Other problems, such as lawn mowing, operate on a quasi-static environment, allowing robot actions to be planned much farther in advance. Environmental and robotic constraints also significantly affect the types of algorithms used. For example, a slower omnidirectional lawnmower will typically choose a different coverage strategy than a faster mower with nonholonomic steering. An omnidirectional mower may use a simple rectangular graph search algorithm, while a nonholonomic vehicle would tend to use more complex lattice planner.

The nature of the coverage criteria also strongly impacts the type of algorithms considered. A surveillance robot that covers an area by pointing a camera at a location from any of a near infinite number of vantage points will require different planning techniques than a vacuuming robot which covers an area by simply traveling over it.

BRIEF SUMMARY OF THE INVENTION

The system disclosed herein precisely maneuvers one or more machine vision components and/or one or more surface processing devices over the surface of a three-dimensional object. The vision systems gather data about the surface that are used to inform the surface process. These data include both intrinsic properties of the surface, such as color, texture or abstract classification results, along with precise estimates of the distance and orientation of the surface relative to the processing point. These data are used to accurately plan for and modulate the surface process to efficiently generate high-quality results. In the preferred embodiment of the invention, the machine vision components are comprised of multi-spectral cameras with corresponding illumination sources that can discriminate between various layers of paint and underlying substrates, and the surface processing device is a high-power laser scanner, originally designed for laser welding, which is used to remove coatings from aeronautical surfaces.

DETAILED DESCRIPTION OF THE INVENTION

Figure 1:
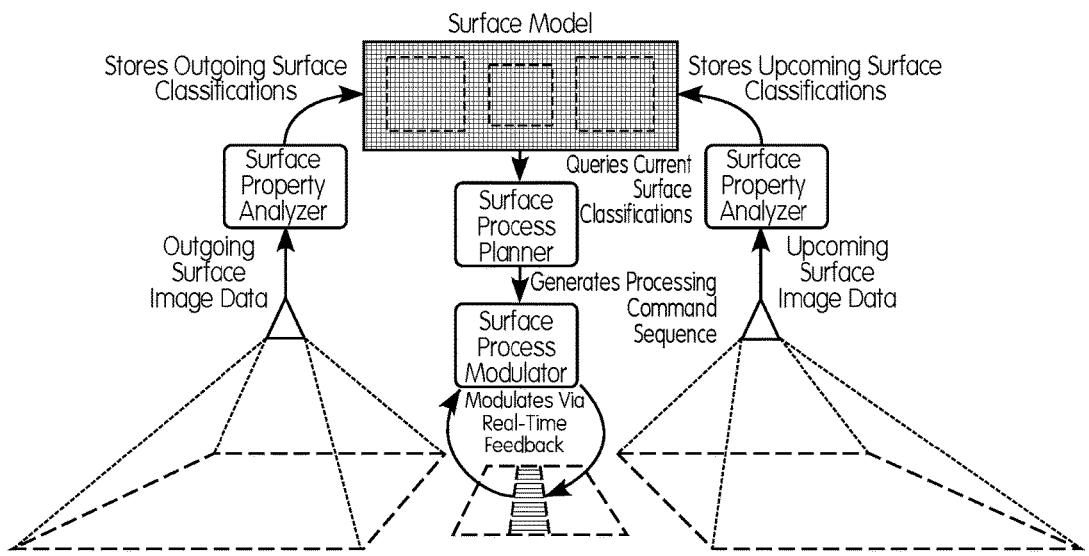
FIG. 1: Core Operational Principles. The symmetry of the Surface Property Analyzers allows surface classification data to be generated both immediately before and immediately after processing.

In one embodiment, the system can maneuver two machine vision components and a surface processing device over the surface of a three-dimensional object. The vision system is meant to gather sufficient data about the surface passing beneath the processing point to accurately plan for and modulate the surface process to efficiently generate high-quality results. In the case of the currently-implemented system, the surface processing device is, in one example, a high-power laser scanner, originally designed for laser welding, which is used to remove coatings from aeronautical surfaces, and the vision components estimate both the present state of the surface, i.e., where there remains coating to be stripped, and the distance and orientation of the surface relative to the aforementioned high-power laser scanner The central use case of continuous surface processing is captured in FIG. 1, showing the principal collaborations between five critical system components and the target surface; These five components, discussed in detail below, include:

Surface Property Analyzer
Surface Model
Surface Process Planner
Surface Process Modulator
Surface Coverage Planner Two Surface Property Analyzers process image data both before and after the processing point to generate classification information relative to the active process. In the case of laser coating removal, this means classifying the surface as one of "topcoat", "primer" or "substrate", where the first two imply that some amount of processing remains to be done, and the last implies that processing is complete. These results of the surface analysis are stored in the Surface Model, where the data from "before" the processing point are used to by the Surface Process Planner modulate the surface process, and the data from "after" the processing point are used to inspect the results of the process, and, in the example of coating removal, to determine whether additional passes are required.

The Surface Model captures the complete surface geometry and caches classified state of the target surface in a persistent database associated with the physical object undergoing surface inspection or processing.

The Surface Process Planner queries the most recently observed SPA data from the target surface immediately along the trajectory of the processing tool to plan a sequence of processing actions. This series of actions is passed to the Surface Process Modulator.

The Surface Process Modulator combines the commands from the Surface Process Planner with real-time feedback to yield finer control of the overall process and a higher-quality end result. In the case of laser coating removal, this means modulating the laser intensity depending on the reaction of the surface to the previous laser command.

Figure 2:
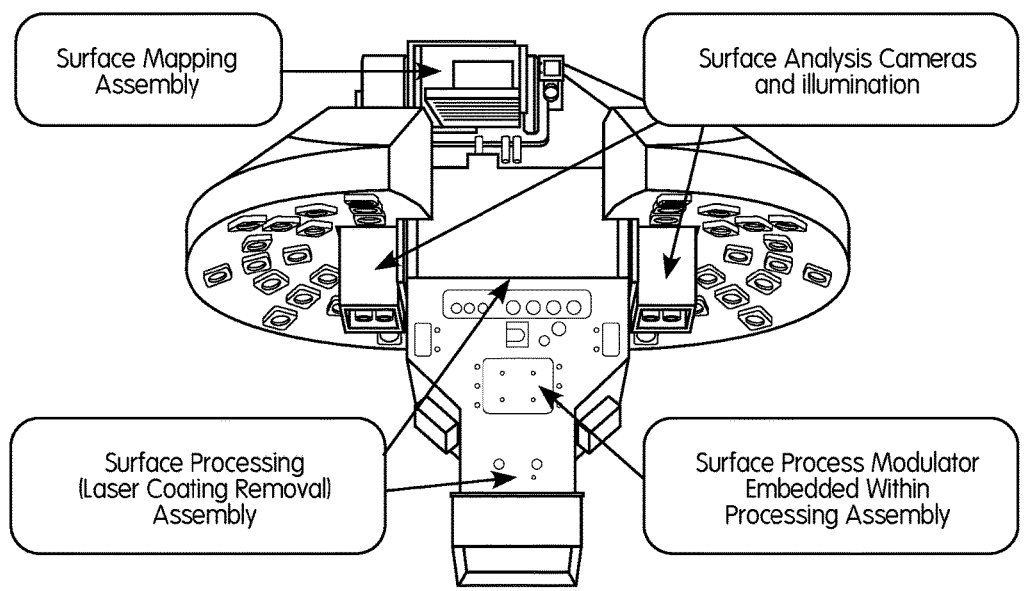
FIG. 2: End Effector for laser coating removal, including all components described in FIG. 1, plus a surface mapping unit and other support components for the laser coating removal process.

The present implementation of this system combines these components, and more, into a custom end effector, shown in FIG. 2, which is mounted to, for example, an industrial manipulator to allow precise positioning and smooth motion relative to the target surface.

To enable consistent performance over a wide variety of objects, this system takes a strongly model-centric programming approach, generating plans, storing perception results, and otherwise specifying system behavior relative to an explicit model of the target surface, as suggested in FIG. 1. As such, the ultimate accuracy and effectiveness of the system depends heavily on the construction and maintenance of a highly accurate model of the target surface geometry, its present state, and, most importantly, its precise position relative to the robot.

Figure 3:
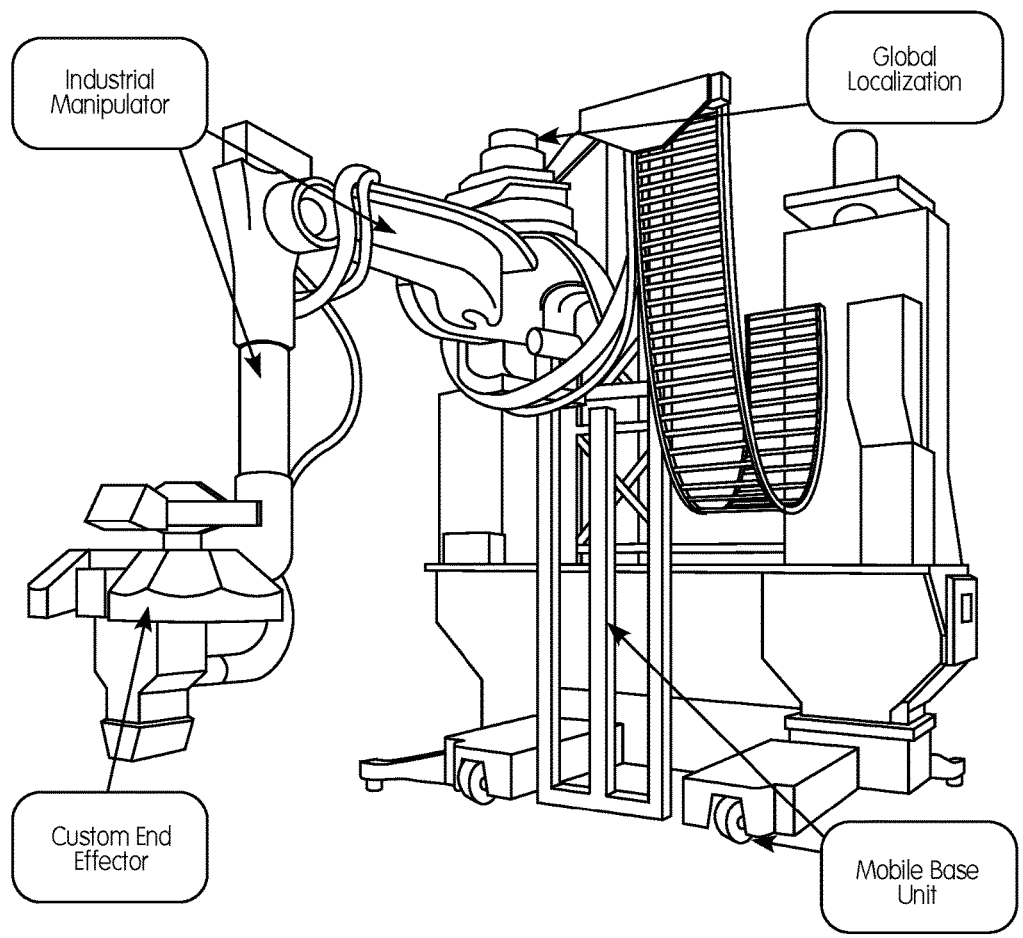
FIG. 3: Complete mobile system for automated surface processing.

Given an accurate geometric model of the surface of a three-dimensional object, the Surface Coverage Planner plans maneuvers for the industrial arm that efficiently cover the entire target surface while respecting the geometric and temporal constraints of the surface process. In concert, the components described above are sufficient to process the entire surface area of relatively small target objects that are completely reachable from a single, fixed manipulator location. The amount of reachable surface area is extended by mounting the manipulator to a Mobile Base Unit, such as the one shown in FIG. 3, allowing the manipulator to be repositioned to various locations around larger objects, such as aircraft, as necessary to reach the entire surface.

In one embodiment, the Surface Model represents the surface of a three-dimensional object as a set of homomorphic two-dimensional manifolds, called "Surface Patches". To maintain homomorphism, which is to say that distances in the 2D manifold map strongly to the same distances over the 3D surface, and angles between vectors in the 2D manifold are preserved when mapped into 3D space, each individual surface patch must have several important geometric properties:
  The patch should have locally contiguous geometry, which is to say that the patch is continuous to at least the second order (no discontinuities through C2), and
  If curved at all, there should be a single "dominant" direction of curvature, such as around an aircraft fuselage or along the forward direction of an aircraft wing, such that
  Each patch may be easily "unrolled" with minimal local distortion, thus preserving local homomorphy.

Figure 4:
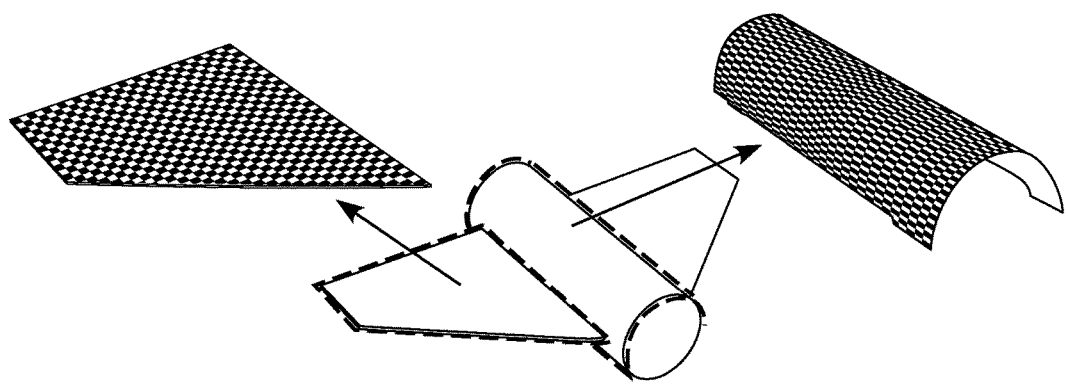
FIG. 4: The decomposition of a full 3D surface model into a set of 2D surface patches, showing wing-top and fuselage-top patches from an example aeronautical structure. Note that this model would include four additional patches (not shown) to cover the other wing top and the three analogous "bottom" surfaces.

These geometric constraints, illustrated in FIG. 4, are very similar to the computer graphics concept of texture mapping. The critical difference lies in the importance of the geometric homomorphism between the 2D "texture" and the 3D model. In a more generic computer graphics setting, local texture distortion can be compensated for by a talented artist, but in this application, the Surface Coverage Planner relies on the local homomorphy to efficiently plan 3D maneuvers in a 2D space.

Each individual patch is further discretized into individual cells, which are analogous to individual pixels in a texture image but, instead of representing color of an arbitrary geometric region, instead represent the detailed state of a physical unit of surface area. Each individual cell encodes its 3D geometry, including the center position and normal, major and minor curvature axes, along with a flexible set of "Surface Properties", which express the state of the surface as relevant to the inspection or processing task at hand. The relevant set of surface properties is dependent on the particular application. In the case of laser coating removal, the relevant surface properties include, for example:
  1. The type of substrate, whether it was most recently classified as "topcoat", "primer" or "substrate", and when it was last classified as such;
  2. The most recent time that it was exposed to laser energy, and at what intensity;
  3. An array of user-interactive markers that can override the process planning to, for instance:
    Mark a particular area as "virtually masked", which suppresses surface processing in that region, such as to prevent sensitive regions from being exposed to laser energy.
    Mark a particular area as "virtual keep out", which would prevent the surface coverage planner from posing the end effector over an area at all and could be used to compensate for surface obstacles, or, conversely
    Mark a particular area as "requires further processing", such as to override an area that is erroneously classified as "substrate", when the operator can see that it is simply an anomalous paint color or other surface anomaly.

All such surface data are stored in a database that is accessible to the entire system, so that the detailed geometry and state of the target surface may be queried by any system component at any time. This directly supports a wide variety of perception, planning and analysis tasks while maintaining a good Model-Controller-View separation of concerns. The model may also be archived for offline analysis, such as to compare results with those of other same-type aircraft, or even to the same aircraft on subsequent visits to the processing facility.

In one embodiment of the invention, model generation is a manual process that begins with the construction of a prior model, which either be generated by hand or can be derived from existing 3D models, but has several constraints on its composition. In the simplest case, the prior model can be comprised of a single, closed 3D geometry that represents the "outer mold line" of the object to be worked upon. That is, surfaces that are physically contiguous must be represented by contiguous geometry, which, while straightforward at first glance, is counter to the construction of most existing 3D models. For example, adjacent or overlapping physical components, such as control surfaces attached to a wing, are often modeled as separate geometries to express manufacturing, assembly and articulation concerns. In one example, the base model is generated manually from a combination of existing 3D models and intermediate results from the surface mapping process, relying on human intuition and understanding of the outer-mold problem to generate a model that meets the system's geometric requirements. Given an accurate surface geometry, patch subdivision can be determined, in one example, by using the texture map "unrolling" functionality embedded in professional 3D modeling tools and assigning texture maps to distinct surface patches.

Figure 5:
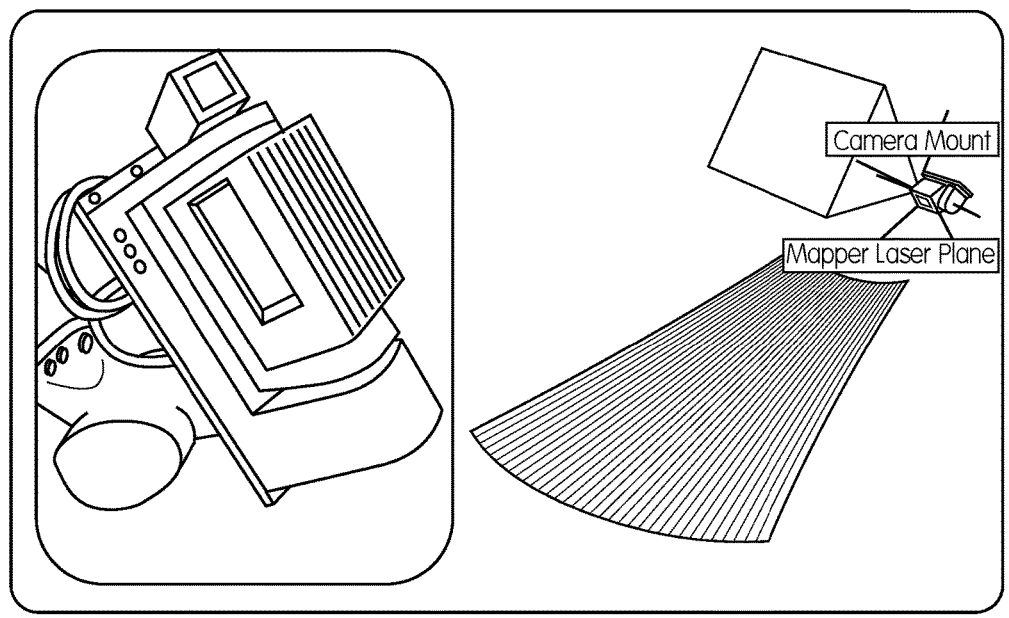
FIG. 5: The mapping sensor mounted on the testing end effector (left) and related CAD model (inset). The relative sensor fields of view are also shown on the right as a frustum for the camera and a laser fan for the Sick LMS400.

In one embodiment, Surface Model generation and localization are performed using data from a three-dimensional range sensor, such as traditional LIDAR, Active Stereo Projection, or Flash LIDAR. The present system uses a 3D ranging sensor constructed by mounting a two-dimensional planar scanner on a custom tilt mechanism that sweeps the measurement plane through the third dimension, as shown in FIG. 5. The tilt mechanism includes a color camera with a horizontal field of view similar to that of the planar LIDAR scanner, which enables the augmentation of the resulting range data with surface color and texture information. The mapping sensor is included in the End Effector shown in FIG. 2 such that it may be maneuvered with the same industrial manipulator in order to acquire range data of the target surface from multiple vantage points.

In one embodiment, the process of capturing a single scan of the surface, called a "point cloud", consists of:

1. Selecting a desired vantage point for the mapping sensor, such as to acquire data from a region of the target surface that has not yet been measured;
2. Commanding the manipulator to pose the mapping sensor at that vantage point;
3. Waiting for the manipulator to complete the maneuver, plus a small delay to allow any dynamic side-effects of the motion to settle out;
4. Commanding the mapping sensor to smoothly sweep its tilt mechanism through a desired range, collecting LIDAR data continually through the sweep;
5. Iteratively commanding the tilt mechanism to individual positions along that sweep and capturing color image data that covers the same angular range as the LIDAR data; and
6. Returning the tilt mechanism to a nominal "home" position.

The process above may be iterated multiple times, from multiple vantage points, and from multiple Mobile Base locations, to capture data from much larger surfaces than are possible from a single pose of the mapping sensor in isolation. The total system state during each scan, i.e., the pose of the Mobile Base, plus the joint angles of the industrial manipulator joint states, is used to register the resulting point cloud in the work environment's reference frame. These state variables are assumed constant after step #3 above to simplify the overall computational complexity of gathering this "raw" point cloud. However, as with any physical system, both systematic and random errors are present in the derived pose of the mapping sensor, requiring subsequent alignment of such scans.

Figure 6:
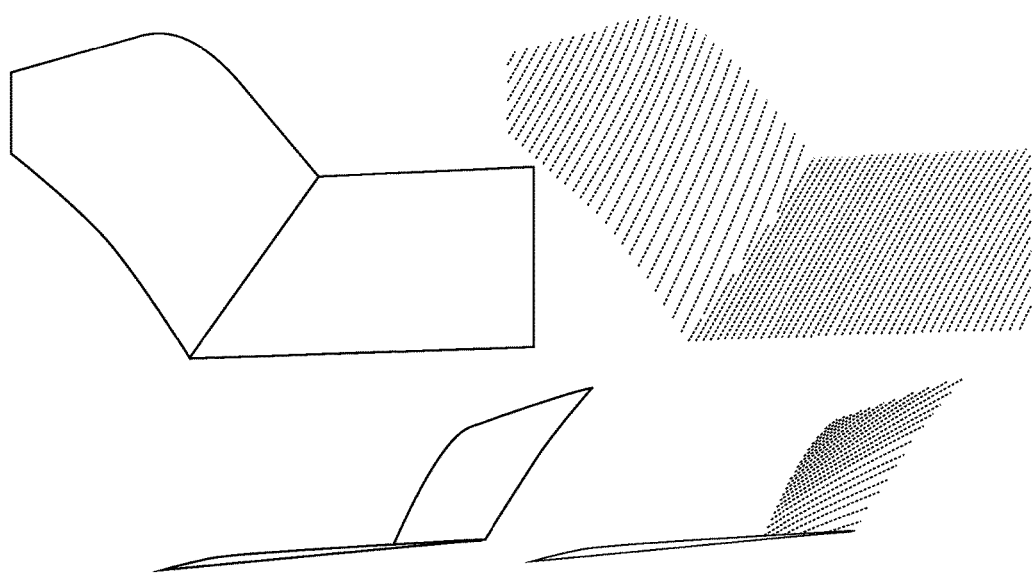
FIG. 6: Typical noisy sensor output results in cloud thicknesses of around 1-2 cm (left). Binning the cloud in angular bins and computing the most likely range for each bin results in a much better estimate of the actual range in a particular direction. Re-projecting the resulting range estimates back into three dimensions provides sub-millimeter cloud thicknesses, significantly reduces the data volume, and maintains an accurate geometric representation (right).
Figure 7:
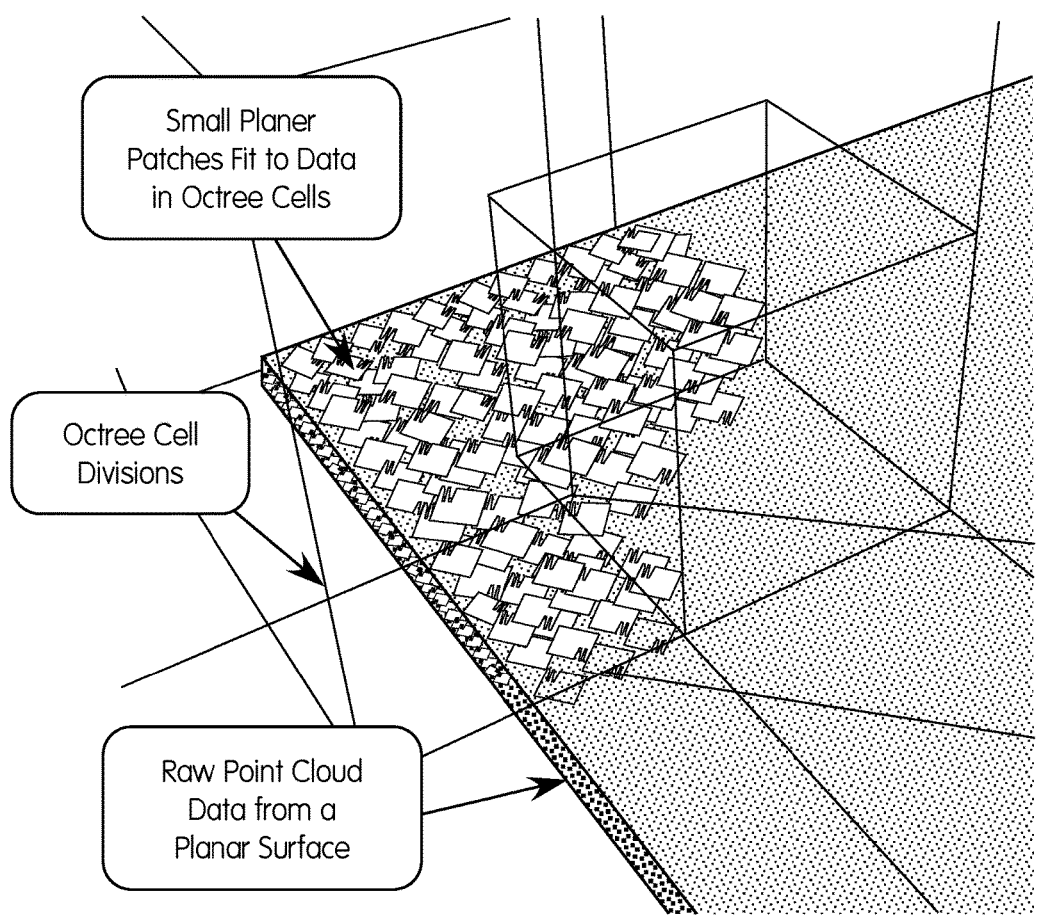
FIG. 7: Octree-based generation of planar patch model. Notice the higher-resolution patches which capture the model detail at the edge of the planar structure, but significantly less data is required to describe the surface.

Each of these point clouds also contains a certain amount of intrinsic sensor noise. As such, the point clouds are post-processed using a maximum-likelihood approach to estimate higher-accuracy range data in an angular binning context, effectively suppressing intrinsic sensor noise as illustrated in FIG. 6. This post-processing step provides both a smoother and more accurate representation of the surface as well as significant reduction in redundant data for downstream processing and display. This algorithm is tuned to the noise characteristics of the specific LIDAR scanner and tilt mechanism currently in use, but can be readily adjusted to use data from any similar three-dimensional point measurement device. It is important to note, however, that the intrinsic properties of the LIDAR scanner heavily influence the quality of the final result, and that increasing errors from the sensor imply at least one of:

A proportional increase of errors in the resulting generated model and localization;
The need to expend more time capturing overlapping scan data in order to reduce the error statistically; or
More advanced algorithm development for modeling and compensating for the inherent noise in the sensor's output.

Given a set of such point clouds with the expectation of some amount of error in their relative poses, it is necessary to perform a refinement step where the data in each cloud are used to align the overall data set into a coherent whole. This is generally observable as an inordinate "thickness" in overlapping regions of scan data, indicating conflicting estimates of the same physical surface. This conflict is resolved using iterative scan matching techniques that incrementally reduce the distance between each point in a given cloud and the surfaces implied by the overlapping regions of other clouds, with the goal of eventually converging on a single, "thinner" point cloud that better estimates the target surface.

These scan matching algorithms generally rely on strong geometric features (e.g., hard corners, edges, or orthogonal planes) to prevent the surfaces from erroneously "gliding" over one another during the matching process. In the context of coating removal on aircraft, however, the generally large, smooth curves of aeronautical surfaces presents relatively few such constraints, making the "gliding" described above a significant challenge. In one example, a novel constraint-finding algorithm, which improves the matching results for point clouds taken of such smooth surfaces, has been developed. The algorithm significantly improves the model generation process by providing higher-quality point cloud matches as inputs to downstream algorithms.

The resulting refined and aligned point clouds are converted into a polygonal mesh that can be imported into professional model editing software and used for, in one example, manual model generation. In one example, the mesh conversion process uses an octree data structure to recursively subdivide the point data into smaller and smaller 3D cells until the points within a given cell can be accurately estimated and replaced with a planar patch. At present, the resulting mesh does not fulfill the requirements on the generated surface model and therefore cannot be used directly. Specifically, this technique does not yield a closed and connected triangulated model, so it can only be used as a guide in the manual modeling process. Nevertheless, this process yields a resulting polygonal estimate of the target surface that has several noteworthy properties:

The sizes of the resulting polygons generally vary inversely to the amount of curvature in a particular vicinity of the measured surface, which is beneficial in that denser, smaller polygons are generated only in areas of particularly high curvature or uncertainty; and
The surface is approximated with far fewer polygons than traditional voxel-based point cloud meshing techniques, which, beyond being a better approximation of the surface; also
Reduces the facet count in the resulting model, reducing the difficulty of the manual process of model manipulation described above.

After the Surface Model has been generated and/or refined, the original globally-registered scan data are used one more time in a localization step, similar to the scan-to-scan matching technique mentioned above, but instead matching the scans to the generated model to refine the model's position within the work environment. This allows the system to more safely operate in much closer proximity to the target surface given a more accurate estimation of the location and shape of the object to be processed.

In one example, the role of manual interaction in the process of refining the point clouds into a representation of the target surface is reduced via a Gaussian probability density distribution that is used to represent the surface, both in support of model generation, and as a constituent of the Surface Model itself. For instance the residual uncertainty of the surface geometry is used to influence the safety standoff distance used by the Surface Coverage Planner to avoid collisions with the surface.

Beyond the scope of model building, small errors in pose estimation for the Mobile Base and Manipulator are also of significant concern for the planning and execution of Surface Coverage maneuvers. That is, the standoff and orthogonality requirements of surface processing require that the end effector be maneuvered very close to the target surface, and inaccuracies in the pose of the arm relative to the surface could lead to any number of problems, including unintended contact with the surface, non-optimal coating removal, or over-burn. As such, immediately prior to planning and executing Surface Coverage commands, the pose of the mobile base is refined by taking several scans of the target surface area to be processed and applying the same scan-matching techniques described above.

Figure 8:
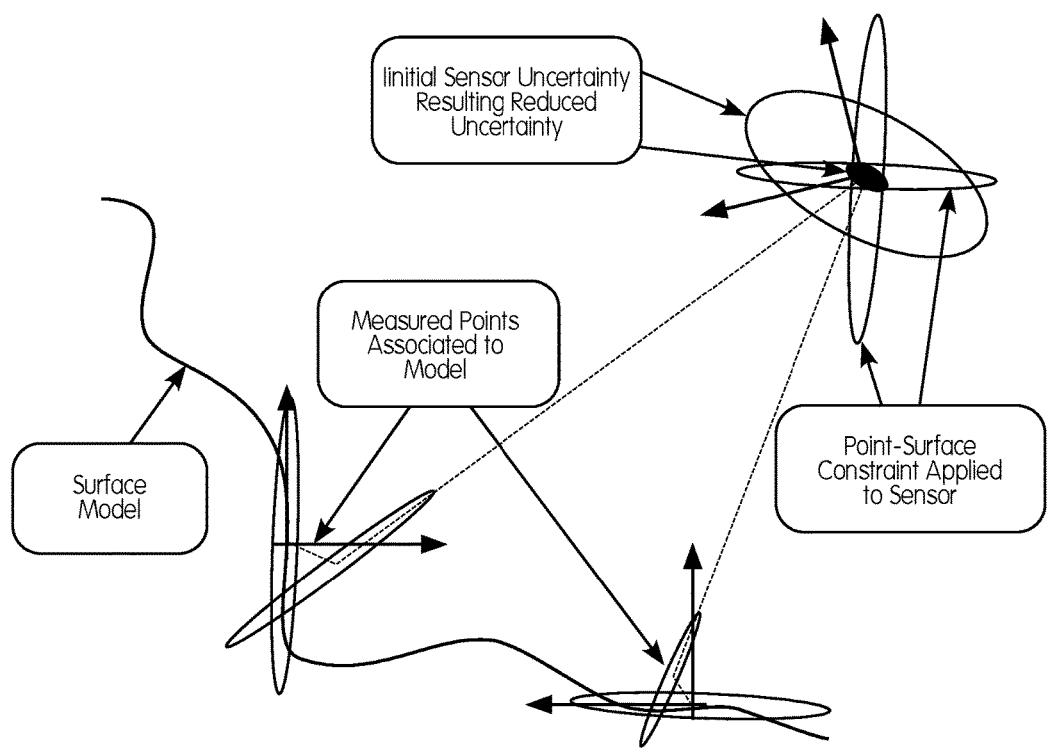
FIG. 8: This illustration qualitatively shows the heuristic used to identify aspects of the surface model which provide strong constraints on the uncertainty of the sensor's pose.

In one example, the sensor poses are planned using a novel next-best-scan technique, which chooses the next scan based on which possible scan will add the most new information regarding the pose of the manipulator's base relative to the target surface. In one example, the information gain heuristic is primarily based on covering the complete target surface geometry with a sufficient density of points, but this heuristic can also be extended to include a more explicit estimate of the reduction in estimated uncertainty of the pose of the manipulator's base relative to the target surface. Thus, the next-best-scan selection can simultaneously emphasize vantage points that constrain the manipulator's base pose while also yielding full overlapping coverage of the surface to be processed. This Mutual Information Gain approach is illustrated for a simple 2D case in FIG. 8 below. The estimated uncertainty of the pose, range measurements, and surface-constrained points are shown as ellipses. For each point on the Surface Model, a Jacobian is estimated relating small perturbations of the pose to the resulting perturbations of the measured ranges. By intersecting the constraints provided by the surface measurements with the uncertainty of the sensor's pose, the pose constraints provided by various measurements of the surface are predicted. This implies the additional information to be gained by making a measurement of a particular portion of the surface, yielding the best next scan based on maximizing the reduction of the sensor pose's uncertainty.

In one example, these resulting scans are matched with the previously built model to estimate the pose of the base of the manipulator during the scan acquisition. This refined pose is published for the Surface Coverage Planner to use when determining the required joint maneuvers to process the target surface. It is noteworthy that this "just in time" surface localization technique blurs the line between pose-estimation inaccuracy and surface model inaccuracy in that the resulting pose can be seen compensating for some combination of both sources of error.

In one example, the next-best-scan selection concepts can be applied to the larger problem of planning and selecting Mobile Base locations, or "stations" to be used for the initial full-surface mapping process. The algorithms described above, in addition to their primary purpose of next-best-scan selection, also express a value function for a base station planner that automates the station selection process and optimizes the time required for initial model-building mapping scans by minimizing mobile base movements along with the number of scans collected at each station.

In another example, the requirements for manual adjustment of the surface model, either during prior model construction or during refinement for use on a particular surface instance, are relaxed, if not eliminated entirely via a set of tools that a non-expert end-user may employ for model building and adjustment. In essence, an initial shell model that captures the gross geometry of the three-dimensional object can be automatically adjusted to fit the geometry of the observed and aligned data where possible, notifying the user of and requesting manual intervention for any non-trivial adjustments that are necessary. This is made possible by defining the surface normals for the base model to accurately describe the direction the surface is allowed to be adjusted and by how much. After the aforementioned stages of data acquisition and determination of a probability density function describing the surface, a numerical regression algorithm may be used to match the surface geometry with the maximum likelihood of a probabilistic surface. This can result in a "most-probable" surface for the user to verify prior to performing interactions around or near the object. A natural extension to this will be to perform similar automated surface adjustment on a smaller scale just prior to close-proximity surface processing, with smaller thresholds on the allowable autonomous adjustments requiring user interaction.

In the majority of coverage problems, the workspace is discretized into uniformly-sized 2D or 3D cells, where each cell represents an area or volume that may require coverage. By using appropriate models, it is possible to estimate which cells will be covered by a particular combination of world state, robot state, and robot action. Coverage planners use this estimate along with a hierarchical system of algorithms to determine a sequence of robot actions that efficiently satisfy the coverage requirements while obeying any process-specific constraints. The nature of these algorithms is strongly influenced by criteria such as the level of environmental uncertainty, environmental and robotic constraints and the nature of the coverage action. Some problems, such as exploratory mapping, operate on a dynamic environment with many unknowns. In these problems coverage planners must plan adaptively in real time, as the "correct" action changes constantly as new information is discovered. Other problems, such as lawn mowing, operate on a quasi-static environment allowing robot actions to be planned much farther in advance. Environmental and robotic constraints also significantly affect the types of algorithms used. For example, a slower omnidirectional lawnmower will typically choose a different coverage strategy than a faster mower with nonholonomic steering. An omnidirectional mower may use a simple rectangular graph search algorithms, while a nonholonomic vehicle would tend to use more complex lattice based planner. The nature of the coverage criteria also strongly impacts the type of algorithms considered. A surveillance robot that covers an area by pointing a camera at a location from any of a near infinite number of vantage points will require different planning techniques than a vacuuming robot which covers an area by simply traveling over it.

The Surface Coverage Planner considers a quasi-static coverage problem in which an implement, such as a laser for coating removal, must be placed over the surface of three-dimensional object. As described above, the surface is mapped onto a set of homomorphic 2D manifolds, which are then discretized along regular grid into relatively small cells. Each cell models the state of an individual area of the surface, including geometry, color, and classification data, as well as other marker that can suppress the requirement for coverage, such as "virtual mask" or "keep out". Coverage is defined to be complete when these surface cells have reached a specified state, such as "primer" or "substrate" in the case of coating removal.

To change the state of these cells, the system moves an end effector over the surface at an orientation, standoff distance, and velocity that are each determined by policies that govern the active surface process. In the case of laser coating removal, a one dimensional swath of cells at the tip of the end effector in FIG. 2 are affected by any one system pose, and the process policies specify a certain surface traversal speed and a minimum "cool down time" that must be observed between subsequent visits to the same surface cells in order to yield acceptable results. Cells must typically be covered multiple times before they reach the desired state, and while an estimation of this number may be available to the Surface Coverage Planner, completeness is primarily determined via sensing by the Surface Property Analyzer that follows "after" the surface processing point.

To move the end effector over the surface, the system employs a multi axis commercial manipulator operating from a well-known base location. This commercial manipulator is defined by a set of forward and inverse kinematics, which translate between individual axis positions and end effector poses. It is noteworthy that most such manipulators are at least partially kinematically redundant, which is to say that while any given set of axis positions will translate into an unambiguous end effector pose, a given end effector pose will typically be achievable by a plurality of axis positions. When planning for smooth end effector motions, this one-to-many inverse mapping is further complicated by singularities in the inverse kinematic space, wherein joints in the manipulator are aligned such that instantaneous motion of the end effector in one or more directions is no longer possible. Beyond intrinsically limiting the motion of the end effector, axis configurations in the vicinity of such singularities are also prone to numerical and dynamic instability, as asymptotically infinite joint velocities become necessary to maintain relatively small velocities at the end effector.

These motions are subject to a number of manipulator, environmental, and process constraints. For example, the commercial manipulator has intrinsic axis position, velocity, and acceleration limits, each of which is reduced by a configurable margin to ensure safe operation and mitigate process noise due to unintended oscillations. Manipulator self-collisions and tether wrapping limits induce constraints which are modeled as complex functions of subsets of axis positions. Environmental constraints include a static obstacle map representing all objects located in the environment such as aircraft, jack-stands, building superstructure, floor, ceiling and wall locations as well as a quasi-static obstacle map representing the base. Process constraints include end effector standoff distance, obstacle standoff distance, ideal coverage velocity, maximum non-coverage surface traversal velocity, and many others.

The Surface Coverage Planner generates a timed sequence of robot states that covers as much of the target surface patch as possible, as quickly as possible, from a given Mobile Base location and subject to all robot, process, and environmental constraints. The most important consideration for this planner is the maximization of active processing time, but it also considers safety, robustness, and completeness as primary motivators.

Coverage problems tend to be intractable in any general form and are typically solved by making simplifying assumptions that allow segmentation of the core problem into a hierarchical set of more easily addressed sub-problems. In one example, the Surface Coverage Planner does this via a novel application of position-based constraints that convert the target surface into contiguous two-dimensional "Solution Manifolds", which contain associated manipulator states and are subject to the constraint that geometrically adjacent surface cells also have joint-space-adjacent manipulator states. This formulation simplifies the problem of covering a three dimensional surface with a six axis manipulator into a simpler two dimensional coverage problem with an omnidirectional "virtual robot" that can transit between any two adjacent cells in a given Solution Manifold.

Figure 9:
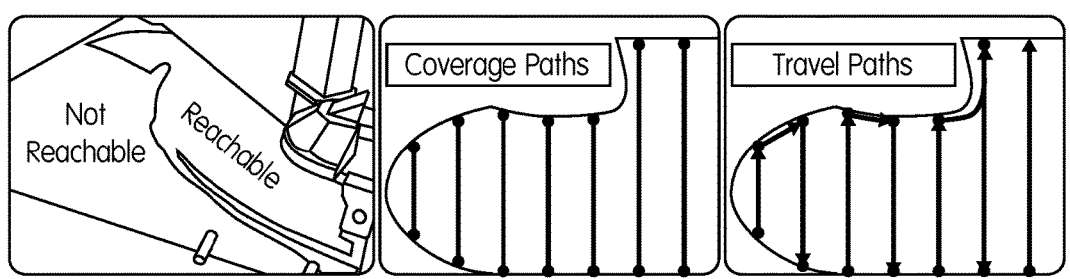
FIG. 9: Surface Trajectory Generation: (Left) A "solution manifold" is generated given the current base location and arm kinematics. (Center) Coverage rows are generated over the solution manifold. (Right) The row sequence is optimized for execution time while simultaneously obeying process policies and constraints.
Figure 10:
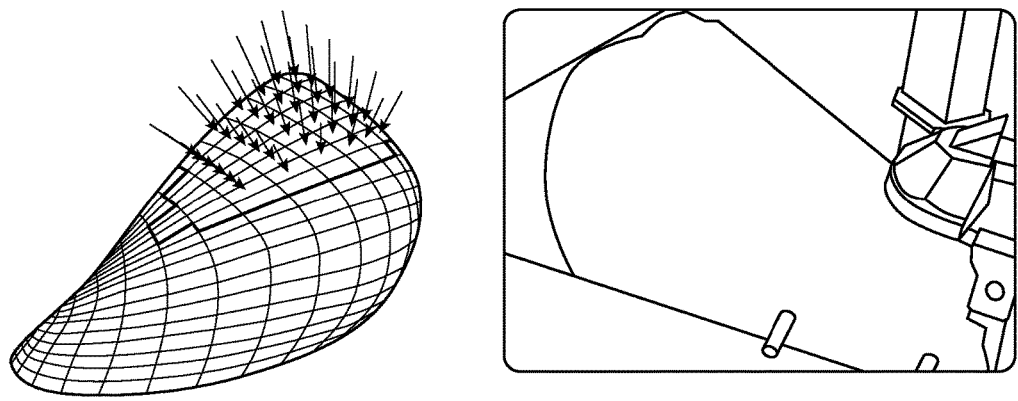
FIG. 10: Solution Manifold Generation. (Left) Surface geometry is used to compute inverse kinematics solutions. (Right) Geographically and physically neighboring inverse kinematic solutions are grown to form "Solution Patches"

Using this representation, coverage paths can be specified by a simple sequence two-dimensional coordinates, and they can be easily generated to efficiently cover the required portions of the Solution Manifold. As shown in FIG. 9, this can be as simple as specifying a set of parallel line segments, with offsets corresponding to the surface processing policies, that cover the entirety of a single Solution Manifold. An optimizer then orders these coverage paths, selects the direction of travel (i.e., forward or backward), and connects their endpoints with optimal travel segments.

These two dimensional paths are then smoothed, blended, and converted to time-based manipulator state trajectories according to the velocity constraints specified by the surface processing policy. Intrinsic manipulator velocity and acceleration constraints are then superimposed on the resulting trajectories via a novel algorithm that "dilates" the time between two trajectory points until all such constraints are met.

In one embodiment, the Surface Coverage Planner is composed of a number of hierarchical, modularized software components which interact to produce complex joint-space manipulator trajectories which safely and efficiently cover a given surface patch.

The Solution Manifold Generator is responsible for creating a two dimensional representation of the surface which can be contiguously "traversed" by the end effector by means of adjacent joint states. It effectively transforms the three dimensional surface geometry at a given surface cell into a corresponding manipulator joint state, assuring:

That individual manipulator states are universally feasible, free from obstacles and self-collisions, and sufficiently far from the aforementioned singularities to avoid their dynamic and numerical challenges;

That adjacent Solution Manifold cells have adjacent manipulator states, simplifying the coverage problem into a two-dimensional search space.

To address kinematic redundancies, as discussed above, several candidate Solution Manifolds are computed for any given combination of base position and surface patch.

What follows is applied to each such candidate, and the manifold that best meets the overall coverage criteria is selected for execution.

The generation of Solution Manifolds is broken down into three primary components: an inverse kinematic solver, a priority queue based nearest neighbor solution patch growing algorithm, and a solution patch weighting and selection algorithm. The inverse kinematic solver computes all valid manipulator joint states which yield end effector poses in satisfaction of the coverage requirements, including compensation for physical effects such as deflection of the manipulator mount on the Mobile Base Unit caused by the torque applied thereto by the mass of the arm in a given joint configuration.

First, the system determines the set of surface poses that satisfy the coverage criteria for each cell in the surface patch. For the de-coating process, these are expressed as tolerances on the high-power laser scanner's standoff from and orientation relative to the surface, yielding a small set of nominal poses for the surface processing device. Within the allowable tolerances, this initial set may be perturbed by small amounts, such as to allow a small deviation in surface standoff or attitude, in order to access otherwise inaccessible areas of more complex surface geometries. These candidate surface poses are computed using a weighted two-dimensional surface regression over both the cell locations and normals, which provides numerically stable, accurate, and smooth surface geometry that eliminates the majority of quantization artifacts that naturally occur in discretized models such as the surface patch representation discussed above.

Once the candidate surface poses have been computed for a given cell, they are transformed from the processing device's reference frame to the native end effector frame for the industrial manipulator. A customized inverse kinematic solver then computes the set of possible manipulator states which satisfy each of the resulting end effector poses, accounting for obstacles, self-collisions, and the estimated base deviation caused by the given manipulator state. Given the redundancies in the current manipulator in combination with the plurality of end effector poses allowed by the coverage policy, it is not uncommon to have sixteen or more inverse kinematic solutions for a given surface cell.

A solution patch generation algorithm then partitions the set of feasible inverse kinematic solutions for each cell into a set of Solution Manifolds, as described above. This is essentially a flood-fill algorithm, starting from the center of the surface patch and connecting all neighboring cells with sufficiently close manipulator states to form an individual Solution Manifold. The determination of "sufficient" proximity in joint space is defined according to the velocities achievable by the given manipulator axis. This flood-fill "consumes" each candidate inverse-kinematic solution as it is incorporated into a given manifold, and the process is repeated for each remaining inverse-kinematic solution until all candidates are assigned to a manifold. The end result is a collection of Solution Manifolds over the target surface which can be arbitrarily large, depending on the complexity of the surface geometry and the nature of the manipulator's kinematic workspace. The resulting Solution Manifolds are sorted by size, and a selection of the largest are processed according to a valuation algorithm which combines:

The current processing requirements for each reachable cell, essentially rewarding coverage of cells that require further processing, with Proximity to the initial manipulator state, which biases the manifold selection process away from solutions that require extraneous arm motions.

The Solution Manifold with the highest score is then selected for further processing. In one example, this "best" manifold is processed in isolation, but it is also possible to define transfer points between overlapping manifolds, effectively joining multiple manifolds into a single, larger Surface Manifold in order to increase the amount of surface that is covered in one pass.

Coverage Path Generator—

The optimal solution manifold is then further segmented into a set of bidirectional paths which satisfy the geometric and dynamic constraints of the surface processing policy. In the case of laser coating removal, this includes a nominal surface traversal speed that limits the amount of laser energy applied to a given unit of surface, along with a "cool-down" period between visitations that requires determination of the surface area affected by the laser at a given pose, and selection of coverage paths that do not expose the same area to laser energy within a configurable period of time. These constraints are currently accommodated via:

Generating parallel, evenly spaced "rows" along the solution manifold with a fixed offset such that, for example, the surface area exposed to laser energy for any one row does not overlap that of adjacent rows, but In aggregate, the surface area covered by all such rows covers the entire reachable area of the solution manifold, and In the direction of travel for any given row, the inverse-kinematic solutions that comprise the solution manifold satisfy a stricter variation of the proximity rules originally used to generate the manifold and are thus more likely to achieve the required traversal velocity.

Figure 11:
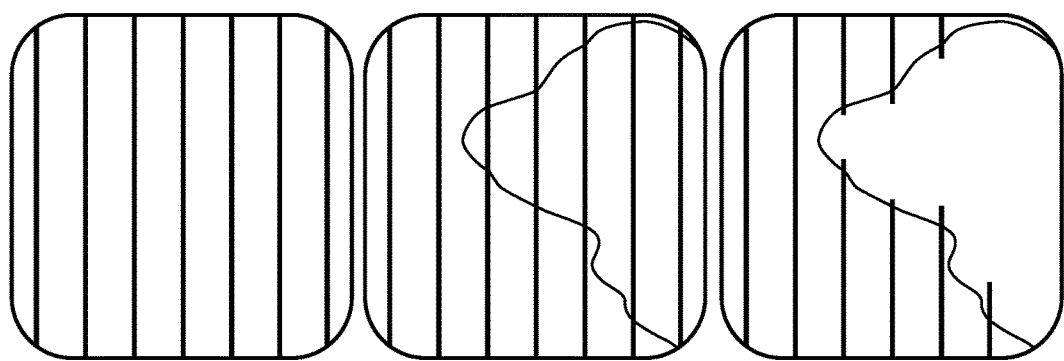
FIG. 11: Coverage Path Generation (Left) A Solution Patch is divided into "Coverage Paths". (Center) Coverage Paths are pruned to eliminate already-completed sections. (Right) The resulting minimal set of coverage paths are extended to allow for end effector acceleration and deceleration.

The first two requirements directly represent the solution to the coverage problem, guaranteeing maximal coverage of the solution manifold, where the third strengthens the guarantee of smooth linear motion over the surface The resulting set of bidirectional coverage paths, which covers the entire Solution Manifold, is then pruned for efficiency as illustrated in FIG. 11. Sections which cover surface cells that are already "complete" according to the surface processing policy are removed, leaving only paths covering incomplete regions. This optimization step increases active processing time by allowing the end points of active rows to be connected with paths that either short-cut to adjacent rows or traverse the surface much more quickly than would otherwise be allowed for active processing.

Coverage Plan Generator—

The set of optimized coverage paths are then assembled into a single coverage maneuver by a combination of traditional and novel graph search algorithms. The first, more traditional component is a standard application of Djikstra's algorithm to a rectangular connectivity graph to compute the cost and optimal path between any two points on the solution manifold.

The second component, called the "Coverage Path Optimizer", is an optimizer that determines a near-optimal ordering of and traversal direction for each coverage path by expressing the problem as a binomial generalized traveling salesman problem. Each path is thus expressed as a set of two "cities", one for each traversal direction, where visiting either one marks the entire path as "visited".

Initial city to city costs are generated using optimal path costs from the aforementioned graph search planner, and are subsequently modulated by any temporal parameters of the surface process. In the case of laser coating removal, this modulation consists of an artificial increase in the cost of traversing adjacent rows that are "too close" and violate the thermal cooling requirements of the laser process.

After the coverage paths ordering and direction has been optimized, they are connected via the traditional graph-search techniques described above, resulting in a continuous set of surface manifold coordinates, labeled as either "coverage" or "travel" as in FIG. 9, which the end effector should follow to completely cover the required portions of the solution manifold.

Robot State Trajectory Generator—

The Robot State Trajectory Generator converts the optimized coverage plan from a list of two dimensional surface coordinates into a temporal sequence of manipulator states that satisfy both the surface process velocity requirements and the intrinsic manipulator velocity and acceleration constraints. During this stage, the resulting trajectories are also filtered to reduce aliasing effects due to graph search over a discretized surface, and to replace "hard" corners in the transitions between coverage and travel segments with smoother transitions that maximize active processing time while minimizing undesirable system oscillations.

The first of two such filtering stages consists of a surface-space algorithm that applies an adaptive quadratic regression to a rolling window of the surface trajectory in order suppress the aforementioned effects of aliasing in surface space. This algorithm includes adaptive parameterization that allows smoothing to occur while still obeying underlying system constraints, such as manipulator self-collisions or the observance of "keep out" regions.

Figure 12:
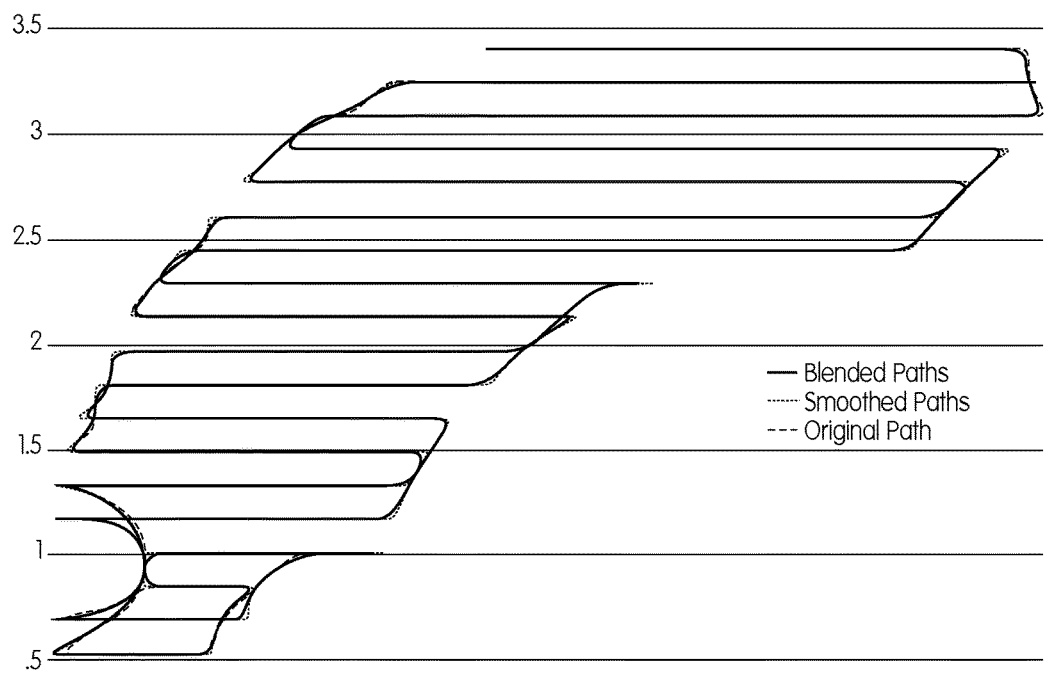
FIG. 12: Coverage Plan Smoothing

These smoothed paths are then passed through an adaptive blending algorithm, which uses a sinusoidal weighting scheme to round off the connection points between coverage and travel paths, yielding a spline-like final surface trajectory, as illustrated in FIG. 12. This stage increases active processing time by replacing the quasi-static junction between coverage and travel paths with a fully dynamic trajectory that reduces, if not eliminates, the requirement to slow to a stop in order to change traversal direction on the surface.

Once a smoothed coverage plan is generated in 2D surface coordinates, it is converted into a valid manipulator joint-space trajectory by indexing through the Solution Manifold to retrieve the corresponding inverse kinematic solutions. An additional form of two-dimensional quadratic regression is used at this stage to suppress undesirable oscillation due to surface discretization or numerical precision, and the time interval between each manipulator state is derived by computing the target end effector velocity as a function of the current surface processing policy.

As a final processing step, the resulting joint-space trajectory is subjected to a suite of constraint-based time dilation algorithms that iteratively expand the time between adjacent states in the surface coverage maneuver to enforce:
  A safety-critical maximum end effector speed, which is configured to 500 mm/s in the current embodiment
  Configurable joint-space velocity limits for the manipulator
  Configurable joint-space acceleration limits of the manipulator The application of these constraints in this order maximizes the end effector surface velocity at any given instant, which in turn maximizes active processing time, which is a key performance parameter for this system.

Surface Ingress/Egress Planner—

The final step in constructing a full surface coverage maneuver is to generate paths that connect the initial state of the manipulator to an appropriate point in the on-surface trajectory, and similarly return the manipulator to its initial position when surface processing is complete. These maneuvers, called "ingress" and "egress" maneuvers, are planned in the much the same manner as generalized arm motions, with a special exception made for planning failures. In such cases, alternate ingress and egress points are substituted until both plans succeed, and travel paths are added to the on-surface trajectory as necessary to connect to the original coverage plan. As an additional safety mechanism, the time dilation algorithms described above are extended with a "soft landing" rule that slows the speed of the end effector in the vicinity of the surface to mitigate the risk of "plunging" oscillations that may compel surface collisions and to generally increase end-user comfort with the system's operation.

Plan Verification and Metrics Suite—

Before publication to the manipulator control task, the trajectory undergoes one final validation step, using a highly conservative variation of the obstacle detection mechanisms as a mitigation of the risk that algorithmic or numerical errors in coverage path generation can yield a path that would collide with the surface. This is especially prudent when operating industrial manipulators within centimeters of potentially valuable target surfaces.

Various performance metrics are also computed as a side effect of the plan validation process that capture the extent to which the resulting plan maximizes active processing time, along with detailed enumeration of any sources of inefficiency, informing both end usage and ongoing engineering efforts of the present capabilities and principal inefficiencies of the overall system.

Failure Recovery—

For systems that are ultimately intended for long-term industrial deployment, robust detection and treatment of failures is a critical design issue. Given the complexity of the Surface Coverage Planner, coupled with its highly conservative surface safety rules, there is an expectation of intermittent failure due to subtle confluence of errors in base pose, surface geometry, mechanical stiffness, etc. As part of the supervised autonomy paradigm, it necessary to present such failures to the operator for interactive resolution, but it is also necessary to minimize the degree of manual intervention required to address the error. In the case of surface coverage planning, the end user is offered the option to re-run the surface coverage command with a set of supplemental strategies that are designed to overcome typical failure cases. An example of such a strategy would be to temporarily reduce the degree of conservativeness applied to the obstacle checking policies in order to extricate the robot from a false-positive "collision" that is an artifact of a transient error in the localization system. Such maneuvers have an increased expectation of operator supervision, and are typically executed at lower speeds until normal operation can be resumed.

Figure 15:
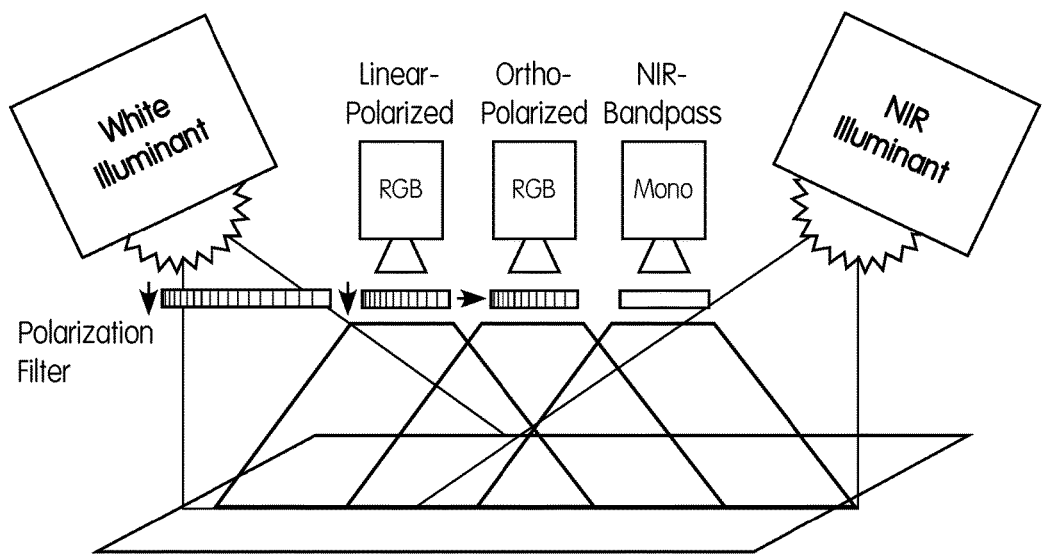
FIG. 15: Functional diagram depicting the current Surface Property Analyzer hardware. On the left, white light is emitted through a polarization filter and collected by two RGB cameras, one behind a collinear polarization filter and one behind an orthogonal filter. On the right, near-infrared light is emitted and collected by a third camera with an appropriate band-pass filter.

While this invention has been described primarily in terms of embodiments using the Surface Coverage Planner to generate a temporal sequence of robot states that cover as much of the target surface patch as possible, those skilled in the art will recognize that the methods of the present invention could also be used for other technologies, such as:
  Extending coverage paths to generic angles across the surface patch (currently they are only in the direction of travel)
  Enabling the row coverage planner to use multiple coverage manifolds in a single plan
  Optimizing various key performance parameters (KPP) (effectively, laser-on time)
  Supporting offline base position planning
  Incorporating sequential based constraints (such as thermal dissipation) directly in the row coverage planning optimizer
  Complete real time adaptive path planning which will modify the coverage paths during the stripping process as new information such as coat thickness is discovered While running a surface coverage plan, all Surface Property Analyzer (SPA) input devices continually capture surface image data and update surface classification information. In the present embodiment, a single SPA device consists of two RGB color cameras and a single near-infrared camera, with appropriate filtration and illumination to yield a 7-channel multi-spectral image sensor, as shown in FIG. 15. These classification results from these sensors are stored in the Surface Model by combining
  The instantaneous pose of the end effector at the time of data acquisition, and
  The geometry and existing classification information embedded in the Surface Model, in order to determine the region of the target surface that is in the field of view.

Figure 13:
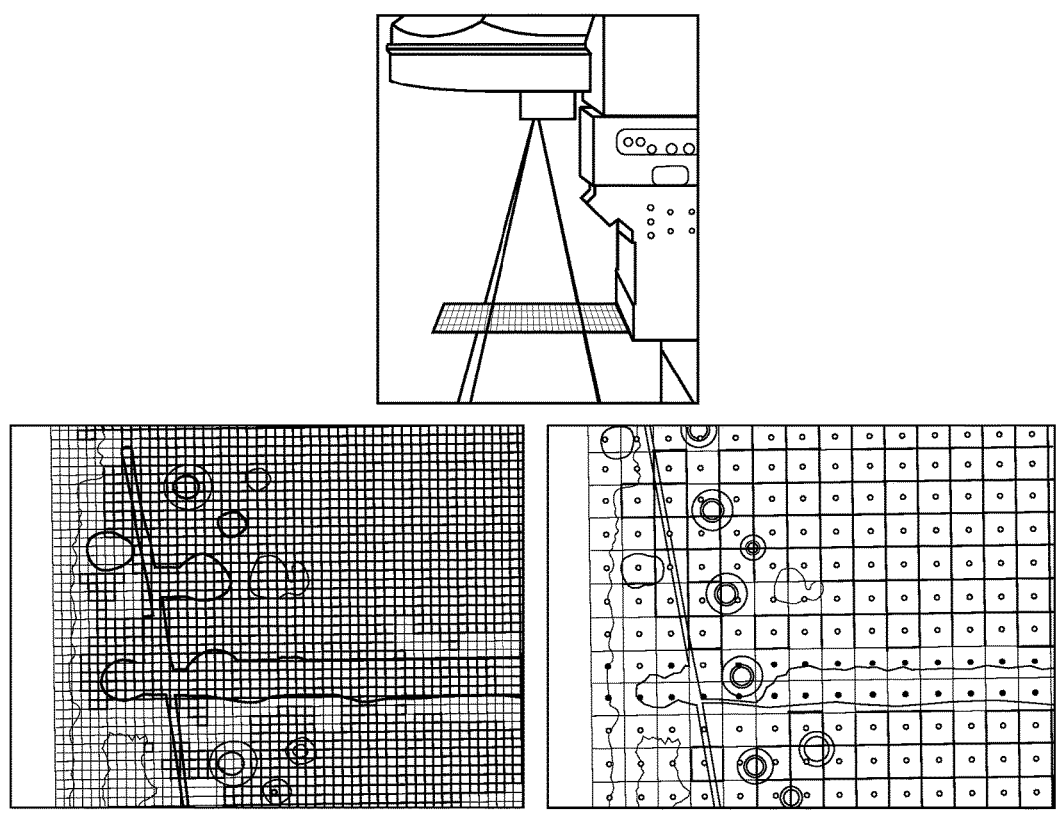
FIG. 13: SPA processing procedure. (Left) Image data are mapped onto the surface. (Center) The data are binned into sub-cellular regions, which are individually classified, represented here by differently colored sub-cell boundaries. (Right) These sub-cellular regions are aggregated according to a configurable policy to yield cell-level classifications.

The surface image data are projected onto the target surface region in order to associate the individual image pixels with the corresponding surface cells to be classified. These pixels are then clustered in to sub-regions for each cell, individually classified on that smaller scale, then aggregated into the final cell classification as illustrated in FIG. 13. The degree of cellular subdivision, shown in FIG. 13 (Center), is presently a four by four grid, or 16 sub-cells for each surface cell. The current system uses a Support Vector Machine (SVM) classification algorithm, which was chosen due to its ability to classify input data at a rate that is largely independent of the underlying model complexity. SVM's are typically used for non-probabilistic binary linear classification, but the standard algorithm is commonly extended to yield multi-class or probabilistic results. In the current embodiment, the SPA algorithm uses such an extension to generate, for each image region, a probability corresponding to each potential classification for that region, e.g., topcoat vs. primer vs. substrate.

The conversion of these sub-cell classifications into the cell-level classifications shown in FIG. 13 (Right) depend on a highly configurable aggregation policy, which can be configured, for example, to depend on secondary features of the target surface, such as substrate type. In the nominal case, a weighted voting scheme is used, based on the constituent sub-cell sizes and their relative classification.

Figure 14:
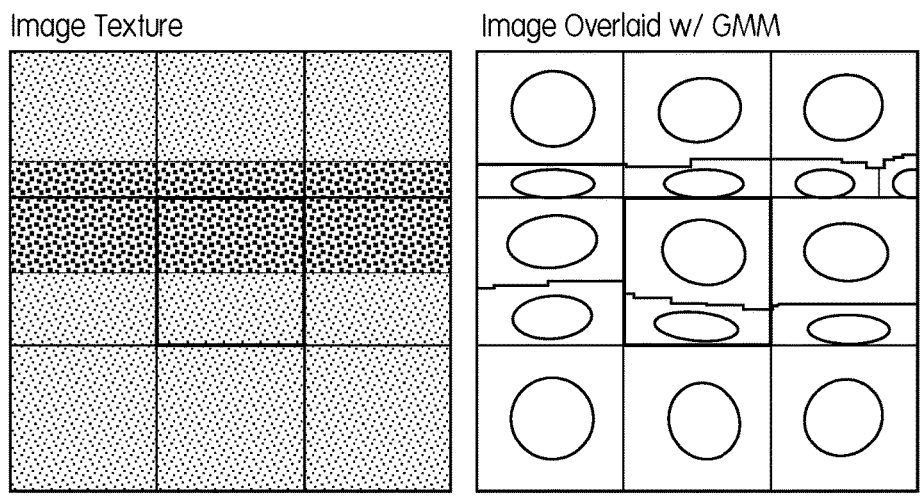
FIG. 14: Side by side comparison of image data and Gaussian Mixture Model classification results.

The aggregation step also produces a Gaussian Mixture Model (GMM) in order to retain some information about the sub-cellular distribution of surface classifications. This has the distinct advantage of being an explicit expression of the idea that, at any level of discretization, a given surface cell will generally contain a plurality of surface classes, and that the approximate distribution of those classes is useful information to downstream consumers. The example GMM data in FIG. 14 shows the potential benefits of using this representation to overcome cell-aliasing and quantization issues. As such, the Surface Processing Planner exploits of this alternate representation to generate higher-fidelity processing commands at the sub-cell level.

While the Surface Property Analyzer's algorithms have been described primarily in terms of its use of Gaussian Mixture Models to express the classification information from a single set of SPA image data, those skilled in the art will recognize that the methods of the present invention could also be used with other technologies, such as:

Improving the accuracy of GMM generation by using overlapping regions from other SPA image data sets;

Application of alternate sub-cellular segmentation algorithms, such as using a non-Gaussian basis function for creating sub-cellular regions, such as to generate explicit geometric shapes according to detected features within the image data;

Introduction of alternate classification algorithms (i.e., other than SVM), or using a weighted voting scheme among a plurality classifiers to generate higher-quality results.

Incorporation of a feed forward model into the classification process, which could be tuned to combine information from SPA image data with the expected effects of any processing that occurred since the previous observation of a particular region of the surface.

The usage of the SVM classifier allows a wide variety of sensor data to be applied to the classification problem, allowing the SPA to be easily reconfigured to classify for different surface processing tasks, given a sufficiently discriminative set of sensors and associated training data. For laser coating removal, the current implementation makes use of three cameras and associated active illumination sources, as described above and in FIG. 15. The individual color channels from each of these cameras are directly used in the classification algorithm, yielding a seven-dimensional feature space for the SVM: RGB with collinear polarization, RGB with orthogonal polarization, and 850 nm infrared.

The cameras and light sources shown in FIG. 15 are synchronized to ensure that the images from each of the three cameras represent the same perspective and the same moment in time. While not strictly necessary, this reduces the computational complexity of merging the image data from all three cameras in the initial stages of the SPA algorithm. In addition, the cameras and lighting are triggered in complement of the laser coating removal process, which is to say that the images are taken while the laser is off, in order to minimize the effects of light leakage from the laser process.

In addition to standard off-line SVM training techniques, the SPA classification parameters may be interactively updated at runtime. To do so, the operator selects surface cells in a GUI that presents data similar to that shown in FIG. 13, and selects a new desired classification for those cells. The current image data from those cells are then added to the current classification model to produce an updated model. The user can then choose among several options for the updated model, for example:

Preview the classification results for the new model on existing image data in the current patch, Apply the new model to the live SPA classification engine, and/or Save the new model for later use, such as for offline comparison.

This is a critical feature in the final system, as it allows end-users to identify appropriate actions to take on novel surfaces, such as coatings with pigmentation that are not correctly classified by the existing SPA model. As such, advanced GUI tools and a notification scheme are used where the supervisor of the autonomous processing operation is prompted for retraining assistance when the SPA is unsure of the correct classification for a given cell.

Figure 16:
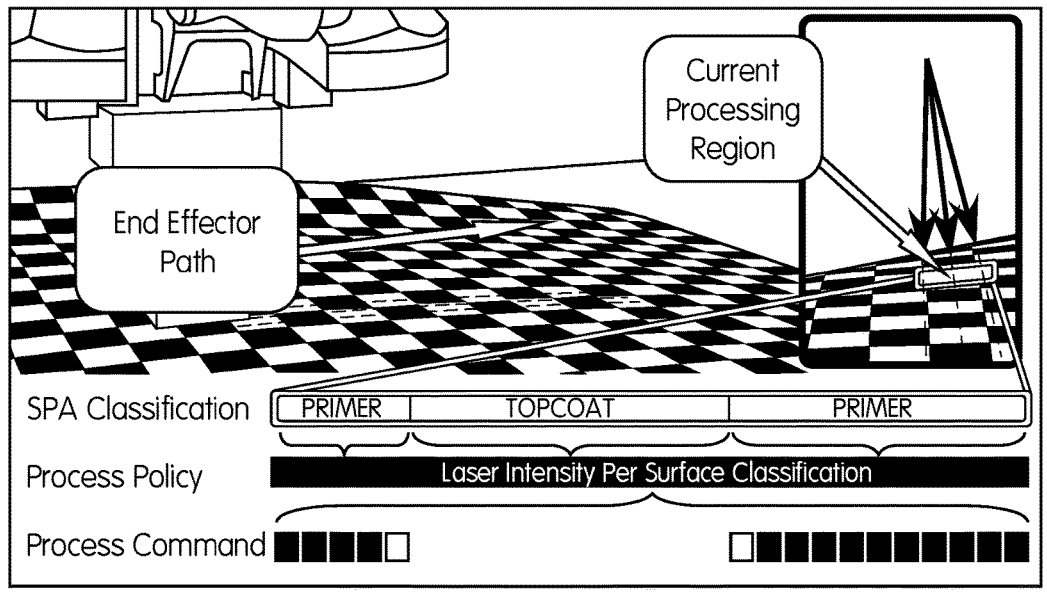
FIG. 16: Surface Planning Process: The current system state and planned arm trajectory are used to determine the region of the target surface that is about to be processed. Associated classification information is retrieved from the Surface Model in order to generate processing commands according to highly configurable policies.

The Surface Process Planner generates regular, time-discretized sequences of surface processing actions by combining, as illustrated in FIG. 16:

The current classification state per unit area as determined by the SPA and as encoded in the Surface Model, The expected motion of the industrial manipulator as intended by the Surface Coverage Planner, Local-frame feedback sensors which provide direct distance and attitude measurements while the end effector is in proximity to the surface, and A set of highly configurable surface processing policies that various requirements for effective surface processing, most notably the appropriate actions to take per surface classification.

Beyond the detailed algorithm for converting surface classifications into processing commands, such as the laser intensities displayed in the example above, the process policies also encode:

The geometric requirements for effective processing, such as surface attitude or standoff distance from the processing tool, which are notably important for laser coating removal, and The terminal conditions for successful completion of the surface process, such as "remove topcoat only", which would imply process termination when all (or at least a strong majority) of the surface has been classified as "primer" or "substrate"

In general, the surface processing policy is expected to generate process commands that will act upon the surface to transform it in a way that will change the surface classification from a state that requires further visiting (a "more work left to be done" state) into a state that does not (a "work completed" state). Depending on the target application, the command generation algorithm and surrounding policies can be arbitrarily complex. In the case of laser coating removal, an example policy would include desired laser intensities to be applied to given surface classifications along with laser focusing and other parameters intrinsic to the coating removal process. The process policy may also encode geometric and temporal concerns, such as the traversal speed of the end effector and cool-down times that will influence the behavior of the Surface Coverage Planner, as discussed above.

Given the expected trajectory of the end effector produced by the Surface Coverage Planner, the Surface Process Planner predicts the location, velocity, and orientation of the processing device over a several-second time. With these predictions, and along that same time horizon, the surface process planner performs spatial and temporal calculations to decide whether and when the various process criteria will be met in the near term. For those times where the process criteria will be met, it then computes which regions of the Surface Model can be acted upon. In turn, the current surface properties associated with those regions are used, via the surface processing policy, to determine the process commands that should be executed as the end effector traverses the surface.

While this is primarily a geometric reasoning problem, the Surface Processing Planner must also support a certain amount of user interaction as well, such as respecting operator-specified masking constraints, or accommodating transient policy overrides, such as to force a coating removal pass in an area that has been misclassified by the SPA. In one example, these features are extended to allow end-users to modify more significant aspects of the surface processing policies, such as the aforementioned surface velocities or laser intensities, to provide more control over the overall process.

In one example, in addition to the loose feedback loop between the SPA units and the surface processing unit, the present system also accommodates a tighter, local-frame feedback control mechanism for the surface process. This feedback control loop operates at a much higher rate and with much lower latency than the machine vision system, and allows for real-time modulation of the process. In the case of laser coating removal, this "Surface Process Modulator" (SPM) consists of several major components:

An array of optical sensors with analog signal conditioning electronics,
Analog to digital converters,
A high-speed digital communication bus,
Process modulation algorithms running on an embedded microcontroller, and
A digital to analog converter to drive the output command to the high-power laser.

Figure 17:
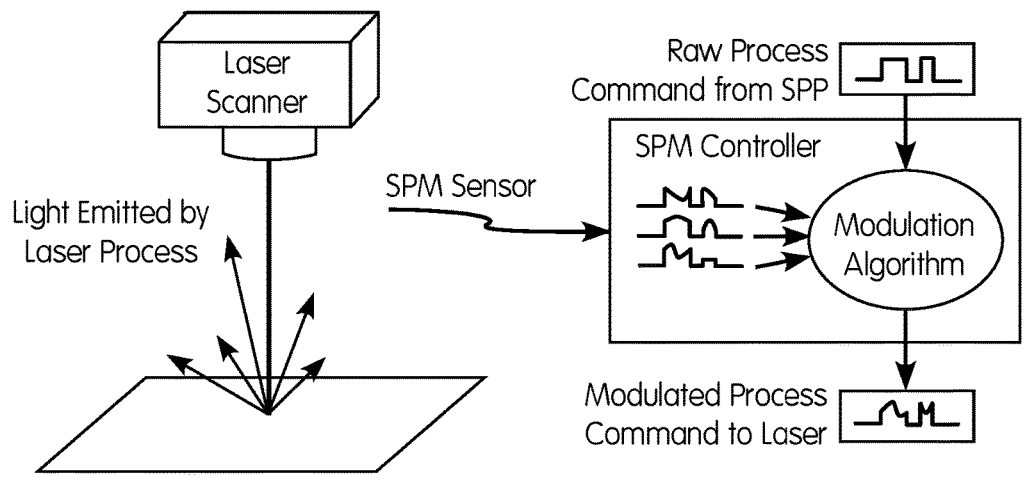
FIG. 17: Block diagram of the Surface Process Modulator for laser coating removal.

FIG. 17 shows a block diagram of the Surface Process Modulator used for laser coating removal. The sensor assembly is mounted in the end effector in such a way that the optical sensors can directly observe the point where the laser intersects the surface, and thus the light given off by the coating removal process. The sensors are photodiodes, each of which is sensitive to a particular wavelength of light and coupled with an analog circuit which generates a voltage proportional to the intensity of the incident illumination. The gain of this circuit can be adjusted on the fly via a software-controlled potentiometer. This allows the circuit to be easily tuned to capture the full dynamic range of light intensity from the surface process. The analog signal generated by each sensor is connected to a high-speed analog to digital converter, in one example capable of 12-bit sampling of each sensor at rates in excess of 250 KHz. This device differs from similar prior arts in that:

1. This device uses an array of optical sensors whose combined field-of-view matches the instantaneous workspace of the present laser coating removal process.
2. This device digitizes the sensor data at the sensor head and transmits the data to the microcontroller over a high-speed digital data link.
3. This device characterizes the response of each sensor across the full width of the laser decoating process and applies both configurable analog gains and a digital normalization function to ensure that the signal response is
4. This device allows a wide array of industry-standard optical filters to be installed to further tune its sensor response to particular applications
5. This device allows for continuous monitoring of sensor responses, online adjustment of analog circuit gains and process parameters, and continual display of computed command outputs over a dedicated TCP/IP network link.

The digital data generated by the ADCs is transmitted via an IEEE 802.3u 100BASE-TX physical layer device, accommodating error-free data rates up to 100 Mbit/s over distances up to 100 m away using standard network cable. At the controller, the digital sensor data are received and processed by an ARM Cortex M4F microcontroller, which combines the signals with externally-specified processing commands in order to fine-tune the amount of laser power to apply to the surface. The microcontroller then commands the desired laser power through a final digital-to-analog converter.

The algorithms used to determine the correct amount of laser power to be applied to the surface based on the sensor readings are highly configurable, and there are two primary algorithms presently implemented in the SPM system. The first is a simple constant-power algorithm that applies a fixed laser power to the surface, which is nominally used during development. The second algorithm uses a set of thresholds applied to the response of a single signal, derived from a combination of the full array of sensors to determine the amount of laser power to command. Those skilled in the art will recognize that the methods of the present invention could readily be extended to use more complex processing algorithms that treat individual sensors differently, for example based on combinations of physical location in the array and installed optical filters.

These algorithms and their parameters may be inspected, selected and adjusted via dedicated TCP/IP communications. Online adjustment of these operating parameters take effect immediately while the system is operating, and they may also be stored in non-volatile EEPROM, allowing the device to retain and automatically load its desired configuration on power-up. The TCP/IP link can also be used to transmit live data from the surface sensors, allowing the user to view the sensor readings in real time while in operation.

While the fundamental workflow described in FIG. 1 can be performed by any reasonably dexterous industrial manipulator from a single fixed location, the typical usage of a fixed base position limits the size of the reachable workspace to the intrinsic capabilities of that manipulator. To enable processing of large-scale work surfaces, this system mounts such a manipulator to a Mobile Base Unit (MBU) that is used to reposition the otherwise fixed base of the arm relative to the target surface. This introduces a host of requirements associated with classical mobile robot navigation, and the solutions incorporated into this system are discussed below:

Localization, or determining the pose of the robot in a fixed, external reference frame;

Manipulator path planning under global obstacle constraints;

Mobile robot path planning and tracking under global obstacle constraints;

Enhanced safety mechanisms and interlocks pertaining to Operator safety in the vicinity of a mobile robot, dynamic stability of the MBU-Arm system, and obstacle model validation.

A combination of sensors and techniques are used in order to localize an individual robot in its work environment, each tuned to a particular operational context. First, and foremost the overall global pose of the robot in the environment is derived using a visual landmark-based localization technique, illustrated in FIG. 18, wherein an array of cameras observe surveyed landmarks, called fiducials. In addition to the fiducial based technique, a surface tracking and registration technique is used when the highest accuracy is required to perform the process.

Figure 18:
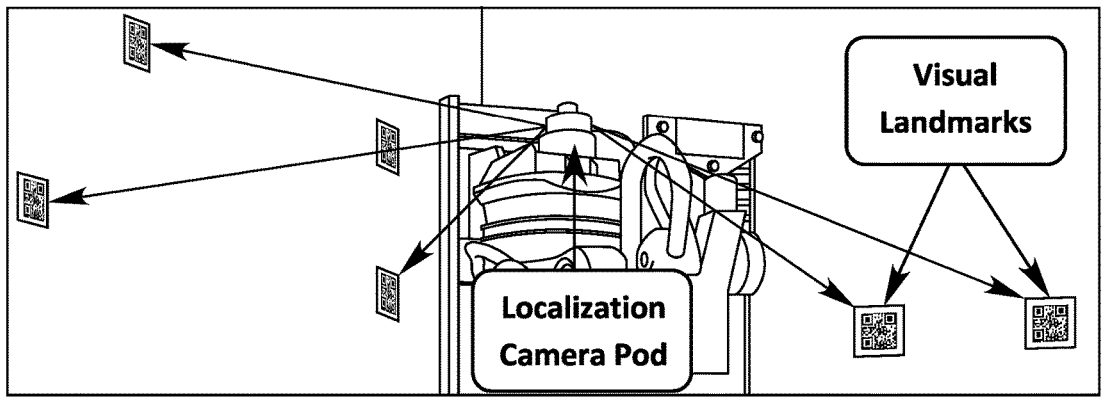
FIG. 18: Global Localization: Cameras on the robot observe visual landmarks (black and white coded squares) with well known (surveyed) locations. Camera placement relative to the base of the manipulator gives full 6-DOF pose.

In one example, the environment markers shown in FIG. 18, called "AprilTags", are designed to be both easily and uniquely identifiable within an image by using pixel encodings that are unique through the four cardinal rotations. That is to say, no tag can be confused with another or with itself in a different orientation, no matter the observation perspective. The initial setup of the localization system consists of:

1. Affixing a constellation of fiducials in the environment such that any given pose of the robot will include a plurality of tags in each camera's field of view;
2. Surveying each fiducial in a manner that associates its unique ID with its full 6-DOF pose in the environment;
3. Affixing a plurality of cameras to the robot (for example, at the base of the manipulator) and determining their extrinsic geometry relative to the robot with high accuracy.

Given these prerequisites, the online portion of the localization algorithm consists of, for each set of image data from the localization cameras:

1. Identify each visible fiducial in the scene and extract its unique ID.
2. Retrieve the surveyed pose of each identified fiducial, and convert that pose into the observing camera's coordinate frame.
3. Seed multiple candidate poses using basic geometric principles of computer vision in combination with the known camera and fiducial geometries.
4. Refine the candidate poses for the multi-camera system via a numerical optimization algorithm by:
   4.1 Using the current pose estimate to project each identified fiducial into its observing camera's image plane (i.e., determine where the fiducial "should be" in the image);
   4.2. Determining the error vectors in image-space between the expected corners of the fiducial and the detected corners;
   4.3. Providing these error vectors, along with pose-to-image-space Jacobian matrices for the observing cameras as the error and gradient functions to the error-minimization algorithm.
5. Select the candidate pose with the lowest error for propagation to the rest of the system.

This technique is selected over existing indoor localization systems due to its capacity to measure orientation very accurately, its potentially very large work envelope, and its capacity to observe structural deflections of the mechanism that connects the plurality of cameras to the moving base. The approach also exhibits relatively low cost, robustness to small errors in the measurement of the environment landmarks, and the ability to compensate for occlusions by simply adding landmarks. The results from the visual localization system are combined with other sensors and localization techniques in a context-dependent manner to determine the instantaneous pose of the system. Other principal sources of localization include:

Odometric, inertial, and other proprioceptive sensors on the Mobile Base Unit,

Surface Localization results from the mapping subsystem.

The degree of influence of each of these sensors on the overall state of the system depends on the operational context of the system, as summarized in Table 1.

TABLE 1

Situational Influence of Localization Sources on the overall State of the Robot

| Operational Context | Visual Localization | MBU Proprioception | Surface Tracking and Registration |
|---|---|---|---|
| Base Stationary (Non-coverage) | Primary | Secondary | n/a |
| Base Stationary (coverage) | None | Secondary | Primary |
| Base Moving | Secondary | Primary | n/a |

The general ideas behind this weighting scheme are that:

1. When the base is in motion, the visual localization solution may be degraded due to camera synchronization issues and/or motion blur, so the Mobile Base Unit's proprioceptive sensors (i.e., dead reckoning via wheel encoders and inertial sensors) should influence the system state more strongly, but
2. When the base is stationary, the visual localization solution is much more stable, so the system state should be most directly influenced by its results, except that
3. Prior to planning a surface coverage maneuver, the system should perform a "just in time" localization of the robot relative to the work surface for maximum accuracy while tracking the shape of the surface.

In one example, the localization subsystem may be augmented by data from other pose sources, such as planar laser scanners or tether instrumentation, to compensate for work areas where significant fiducial occlusion cannot be avoided, such as when working under the wing of large cargo or passenger aircraft.

The Manipulator Planner generates a temporal sequence of robot states that safely transitions the manipulator from a given current state to a specified state while obeying all robot, process, and environmental constraints. These include manipulator-intrinsic position, velocity and acceleration limits, robot self-collision constraints, and a comprehensive environment collision model. The planner is subdivided into two principal components, a multi-resolution collision model and a point to point path planning suite.

Multi-Resolution Collision Model—

Figure 19:
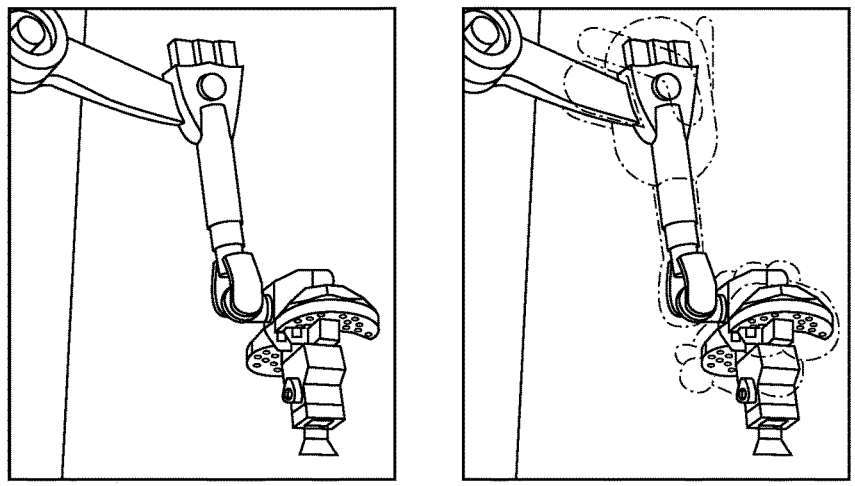
FIG. 19: Multi-Resolution Collision Model Overview. (LEFT) Example manipulator and end effector. (CENTER) Sample manipulator overlaid with "Collision Capsules". (Right) Two dimensional representation of a collision capsule evaluation against the Multi-Resolution Collision Model.
Figure 19:
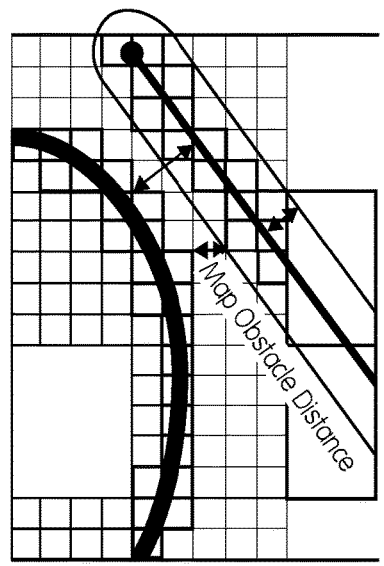

In one example, obstacle avoidance is conducted by means of a two part Multi-Resolution Collision Model. This begins with a discretized, volumetric representation of obstacles in the environment, but expands upon that representation to encode not just obstacle locations, but the distance from each non-obstacle "voxel" to the nearest obstacle. This model is used to process a simplified "enclosing capsule" representation of the manipulator, cable tethers, and end effector, as shown in FIG. 19.

A number of algorithms are used to generate and expand this collision model, including but not limited to:

- A priority-queue-based free cell expansion algorithm which determines the minimal distance of each voxel to the nearest obstacle cell,
- A recursively discretized, voxel based, three dimensional obstacle map,
- A raster search algorithm which scans along a line through the obstacle map to determine the minimal obstacle distance along that line and collect voxels with distances under a given threshold,
- A binomial obstacle search algorithm which recursively bisects a given line to efficiently and accurately determine if a given robot state intersects an obstacle,
- A quasi-interpolation algorithm which uses adjacent voxels to suppress aliasing effects in the discretization process and improve the obstacle distance estimate.

Point to Point Planner—

Figure 20:
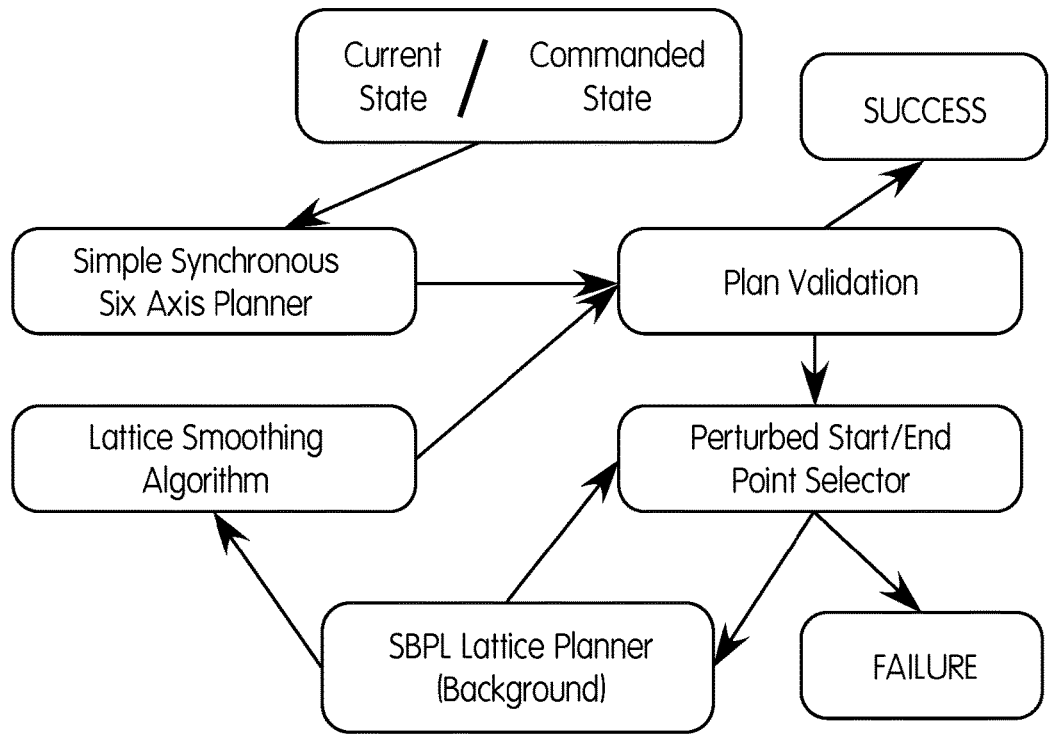
FIG. 20: Point To Point Path Planning Process.

In another example, point to point planning is conducted by means of a hierarchical set of components, arranged as illustrated in FIG. 20. This suite begins with two manipulator states to be connected, specified in joint coordinates and called the "current" and "commanded" states. Given two such states, a simple synchronous joint-state planner uses the manipulator-intrinsic velocity and acceleration limits to generate the fastest possible path between those states. The resulting plan is then checked by means of a plan validation module, which enforces the various speed, acceleration, self-collision and environment-collision rules described above. If this initial, simplistic motion passes those checks, no further work is performed and that plan is selected for execution.

It is noteworthy that the size of the robot's workspace, and the fact that it is generally kept free of extraneous obstacles, allows this simplistic planner to succeed in a nontrivial number of cases, for example, approximately 35-40% in general usage. If the simple plan fails, however, control is passed to an advanced lattice-based planner that generates a more complicated collision-free path to the goal. This begins with a start- and end-point selection module which can provide a variety of slightly-perturbed variations of the original start and end states. This module has two primary functions:

1. Suppress aliasing effects in the lattice planner, which discretizes the joint space of the manipulator for efficiency, but also introduces a problem whereby the "real" start and end points, which are not in collision, may be quantized into neighboring states that are, and
2. Relatedly, any number of correctly-planned robot actions, especially in the vicinity of the target surface, may appear to be slightly in collision in their terminal states due to sensor noise in the localization system and/or small manipulator tracking errors.

In these cases, which include some automated failure recovery scenarios, a variety of initial and final conditions may be generated for use by the lattice planner, each of which being a small "nudge" from the true initial condition. Each combination of start and end configurations is passed to the lattice planner until one such combination succeeds, or until all such options are exhausted, whereupon the failure to plan a safe path is reported to the operator.

In one example, the lattice planner is based on the open-source Search Based Planning Library (SBPL), which employs a heuristically-guided lattice-based search algorithm to generate complex collision-free paths through a given configuration space. As a lattice planner, SBPL generates trajectories that are discretized in joint space and must be smoothed before execution by the robot. The lattice plan smoothing algorithm uses a variation of the simplistic joint-space planner mentioned above to replace as many of the discrete plan segments from the lattice planner as possible with smooth arm motions, while still obeying robot and environment collision constraints. As with all other plan generation sequences, the resulting plan is passed through a final, independent collision model validity check before passing the plan to the controller task for execution.

In one embodiment, the objective of the Mobile Base Motion Planner is to safely maneuver the Mobile Base Unit to place the base of the industrial manipulator at a specified pose in the environment. In general, this pose is specified using a full six degrees of freedom: three Cartesian coordinates and three Euler Angles in the work environment reference frame. In present practice, however, the MBU is a planar mobile robot with hydraulic actuation in the vertical axis. This allows full control of all three Cartesian axes, but only the Yaw angle (rotation about the vertical axis) of the manipulator base can be explicitly controlled. With the height of the manipulator base controlled entirely and explicitly via hydraulic mast, the MBU motion planning problem is primarily a planar mobile robot planning problem.

Figure 21:
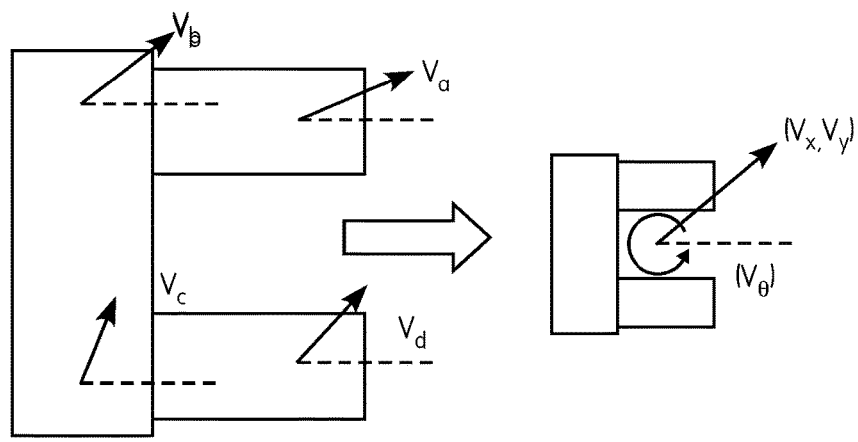
FIG. 21: Mobile Base Kinematics: Wheel angles and speeds can be reduced to linear and rotational velocities in the robot's coordinate frame.
Figure 22:
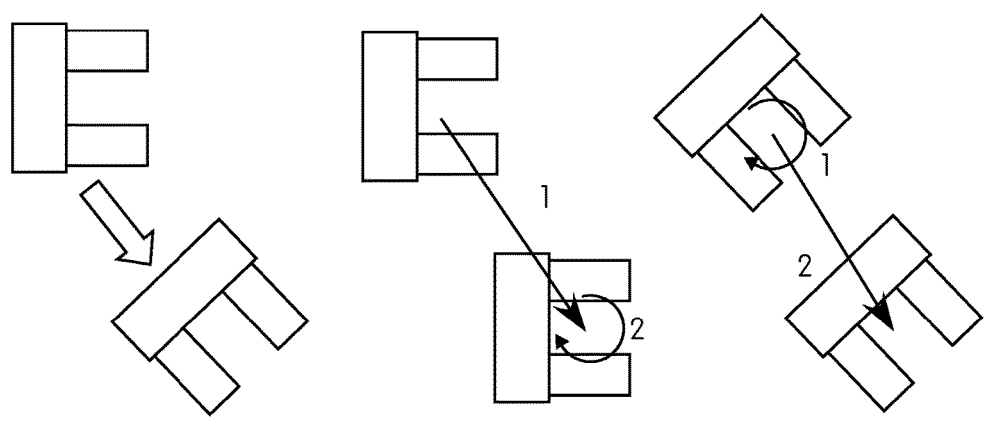
FIG. 22: Simplistic planning for an omnidirectional base: Decompose into combinations of translation and in-place rotation.

As shown in FIG. 21, the MBU is a pseudo-omnidirectional platform, in that, while its motion is instantaneously constrained by the angles of its wheels (i.e., nonholonomic), the wheels are individually steerable such that the platform is capable of achieving arbitrary headings and curvatures given sufficient steering time. This allows for relatively simplistic motion planning, whereby a motion plan is decomposed using a small set of disjoint maneuvers, such as alternating linear translations with in-place rotations to achieve a final goal pose, as shown in FIG. 22.

This basic algorithm, extended with context-specific heuristics such as a sequence of safe intermediate states that allow passage around an aircraft wing, is the algorithm in use at the time of this writing. This yields a small combinatorial space of maneuvers that are each explicitly tested using the same collision model used for Manipulator motion planning. The first combination of maneuvers that passes all obstacle checks is selected and passed to the MBU path tracker, or else the user is notified of a need for manual intervention if all such paths fail the collision checks.

In one example, this motion planner has proven sufficient for initial development and testing of this system, but the present planner relies heavily on manual selection of safe sequences of MBU maneuvers to avoid planner failures. In another example, a more explicit search-based planner is incorporated, using the same underlying planning libraries as are used by the Manipulator Planner, to plan more general paths through the environment. Beyond reducing the reliance on manual selection of intermediate states, this can also help support parallel advancements in MBU station planning.

Figure 23:
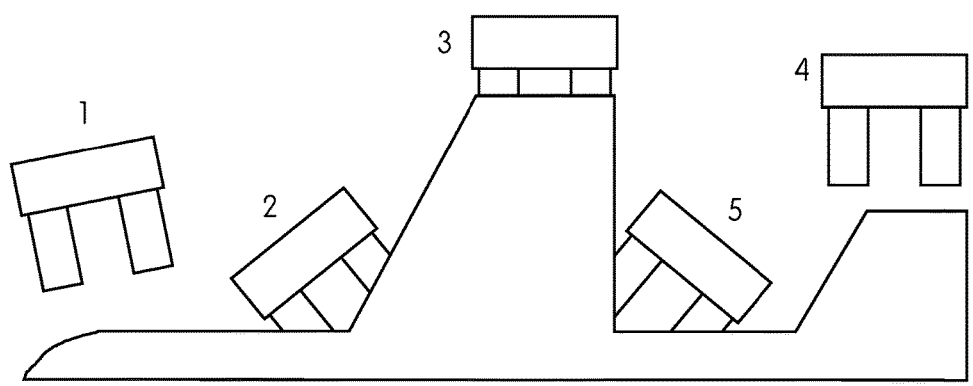
FIG. 23: Example MBU station sequence, covering the port side of an aircraft.

Beyond the ability to plan safe point-to-point maneuvers for the MBU, there is also a need in this system to plan where the MBU should go to accomplish the system's surface processing goals. There are many tradeoffs to consider in the selection of such "MBU Stations", most notably that MBU motion represents time not spent actively processing the surface, which affects the bottom line of any cost-benefit analysis. The essence of the problem is the selection of a sequence of MBU poses that allow the full surface to be processed in minimal time, such as represented for half of an abstract aircraft in FIG. 23.

The disclosed system incorporates several safety features to address the hazards present in a large-scale autonomous vehicle with a high-power laser system. The goals of the safety systems are (in order of priority):

Prevent harm to human operators due to (1) exposure to the high powered laser; and (2) unintended contact with the vehicle.

Prevent harm to the surface being processed due to (1) unintended exposure to laser emission; and (2) unintended contact between the vehicle and the surface Prevent harm to the robot due to: (1) unintended contact with elements of the environment; (2) interference between one part of the robot and another; and (3) instability caused by dynamic maneuvers.

The core of the safety system is an emergency stop mechanism, designed to terminate and prevent laser emission and all external vehicle motion in a fail-safe, highly-reliable way. The safety system follows a basic state machine, with the current operating state of the system clearly indicated to the operators by lights at the operator control station, in the work environment and on the robot. These states, and their implications, are summarized in Table 2.

TABLE 2

Primary states of the Robot Safety System

| System State | Description |
| --- | --- |
| E-Stop | No external robot motion or laser emission is possible, and it is safe for human operators to enter the work area and approach the robot |
| Manual | A trained operator can move either the MBU or manipulator using its COTS pendant. The active device is selected from the safety remote control, described herein, and the other device will not move. Laser emission is not possible. |
| Auto (No Laser) | The software is in control of the vehicle. The software may select to either operate the MBU or the arm. The safety system will prevent motion of the other component. Laser emission is not possible. |
| Auto (With Laser) | Same as above, except laser emission is possible. This state is governed by a key switch at the operator control station whose only key is attached to a safety remote control. |

Figure 24:
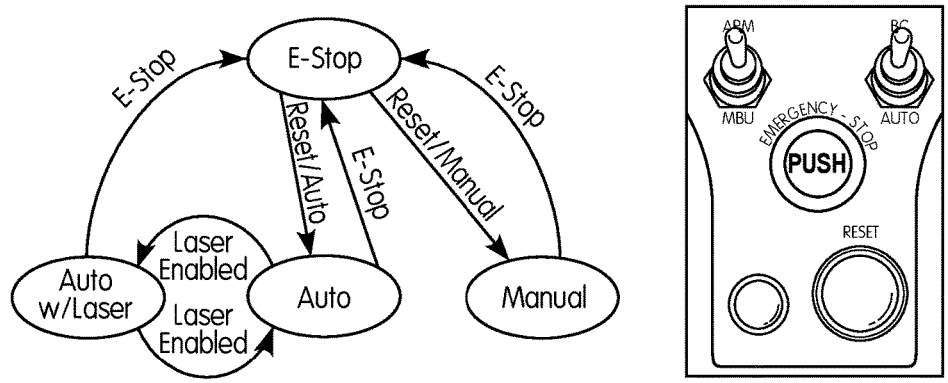
FIG. 24: Safety System state machine and example safety remote.

The transitions between these states are illustrated in FIG. 24. Generally speaking, the triggering of any safety sensor will lead directly to the E-Stop state, requiring operator intervention using the safety remote control to return to an operational state. The various safety sensors used in this system include:

Explicit Emergency Stop Buttons, which are scattered through the work environment as necessary to provide ample opportunity for operators to stop the system.

Door Switches, which are used to implicitly detect a change in the occupancy of the work area. Opening any door to the work area will trigger an E-Stop if the system is in Autonomous with Laser mode, under the assumption that personnel intend to enter the work area.

MBU Tether Limit Switches, which prevents the robot from exiting the work environment or damaging its tether by triggering an E-Stop as the robot approaches the extents of the tether's range.

Dynamic Safety Monitor, which effectively governs the MBU to low speeds by triggering an E-Stop if the MBU exceeds a pre-set speed limit. For example, the MBU in the present system, while capable of speeds in excess of several meters per second, is limited to speeds less than 100 mm/s to be able to guarantee the stability of the combined system.

End Effector Limit Switches, which are built into the end effector and designed to detect contact with any obstacle. Theses switches will be activated if sufficient force is applied to the processing point of the end effector in any direction. If any of these switches are activated, the safety system will enter M-Stop mode and prevent autonomous operation until the end effector has been manually disengaged from the obstacle.

Figure 25:
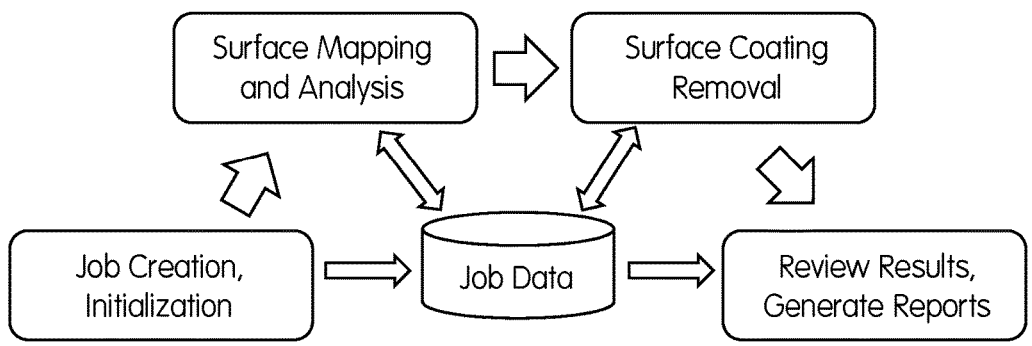
FIG. 25: Principal end user operational model. Blue arrows indicate user-triggered state transitions, and red arrows indicate data flow to and from the Job Model.

The end-user operational model of this system, shown in FIG. 25, orbits a single, coherent "Job Model", which explicitly represents the processing environment, the set of robot systems doing the processing, and the state of the object being processed.

The Job Model may be constructed via interactive wizard, with template jobs available for processing a wide variety of archetypical surfaces in certain default configurations within a given work environment. The job then proceeds through the following sequence of actions:

1. The autonomy supervisor confirms the approximate shape and position of the target surface by comparing the prior model presented in the GUI to the physical surface in the work environment.
2. Upon confirmation, the system proceeds to map the target surface, coordinating the station planning and sequencing activities of one or more robotic systems within the environment with a surface mapping objective.
3. Once all data collection is complete, the robots return to some nominal "home" configuration, and the prior model for the target surface archetype is refined to match the measured target surface, with the autonomous supervisor prompted for appropriate actions to take relative to any anomalous surface geometry.
4. When the model refinement process is complete, the operator must review and approve the deformations and alignment that were performed, selects a desired terminal state for the target surface, such as "remove all coatings", or "remove topcoat only" in the case of laser coating removal.
5. The system coordinates the station planning and sequencing activities of one or more robotic systems, alternately issuing MBU maneuvers and appropriate surface coverage commands until the entire reachable surface area has been transformed into the target state.
    5.1. During execution of Surface Coverage commands, the autonomy supervisor may be queried to provide processing advice on surfaces that cannot be clearly identified by the SPA, and
    5.2. Before a robot departs any given surface processing station, the autonomy supervisor will be given an opportunity to inspect the final results, and optionally to specify additional work to be done on subsets of that area, such as to force "one more cleanup pass" for coating removal.
6. Upon completion of surface processing for each station, all data products, including surface geometry and state, are archived for offline analysis.

In addition to the principal interactions described above, there are several critical operator interactions, part of the supervised autonomy paradigm, which may occur at any time during system operation. Broadly speaking, these events pertain to failure recovery and safety events, the most critical among which are:

1. Unexpected Positive Obstacle Detection, wherein various sensors on each robot are continually measuring the surrounding environment, looking for evidence of solid objects that are not accounted for by the obstacle maps used by the rest of the system. In the event that of such an anomalous obstacle is detected, the system will:

Issue a software emergency stop event for the robot that detected the obstacle, halting any active operations on that system;

Highlight the unexpected obstacle in the GUI, prompting the user for the appropriate action, such as to:

(a) Suspend all active processing in order to allow the user to enter the environment to remove the spurious obstacle, or else (b) Incorporate the obstacle into the collision model and compel all robots to generate new plans that incorporate the new data.

2. System Safety Event, wherein one or more of the safety sensors described above trigger a hardware emergency stop. In this case, the operator will be informed of the ordinal cause of the event and provided with instructions on appropriate recovery actions. This may include using the COTS pendants for the MBU or Manipulator, such as to disengage a limit switch, before resuming manual operation.

Figure 26:
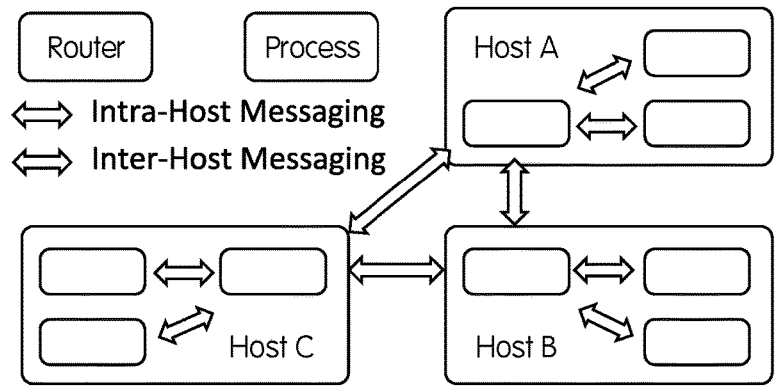
FIG. 26: Cooperating Processes Paradigm: Multiple processes communicate with one another across hosts using hierarchical messaging through message routers.

The fundamental pattern of interaction used in this system is Cooperating Processes, wherein multiple independent programs, distributed across multiple physical systems, collaborate via messaging to achieve the overall system goals. As such, the support software used in this work includes data structures, algorithms, system services, code templates, and design metaphors (in the form of abstracted interfaces) that support the collaboration illustrated in FIG. 26.

In addition to directly supporting the above paradigm, the core infrastructure used in this work also supports pervasive logging of inter-process message traffic, timed playback of those logs, and offline analysis tools that are critical to fault diagnosis and performance analysis in complex software systems.

Figure 27:
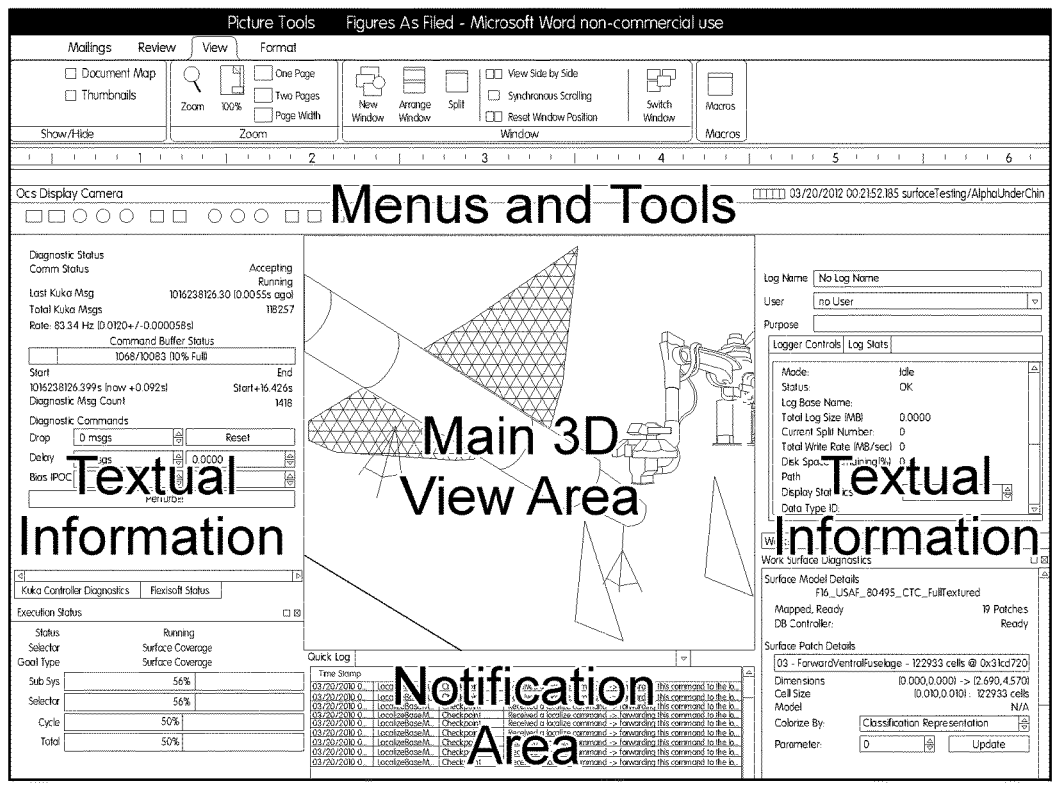
FIG. 27: System User Interface (UI) Metaphor: Plugins provide UI elements for one or more regions and manage them in synchrony with system state.

This system also includes a feature-rich graphical user interface that provides coherent metaphors for visualizing a wide variety of data from and about the system. As shown in FIG. 27, the GUI provides mechanisms for displaying textual information, using standard window metaphors such as buttons and text boxes, along with a rich three-dimensional view of the system state.

Data are visualized in the GUI via a "plugin" metaphor, which allows functionality to be added or removed from a particular GUI instance by adding or removing from the list of active plugins. Following a strong Model-Controller-View separation of concerns, an individual plugin acts as a controller, managing the contents of one or more GUI, or view elements in each area described in the figure above in synchrony with system message traffic, which provides the model. For example, one such plugin may subscribe to the overall system state message, using the data therein to update a 3D model of the system in the center of FIG. 27, but also updating textual information in a side panel, and possibly allowing some basic commands to be issued to the system via buttons on the toolbar.

Figure 28:
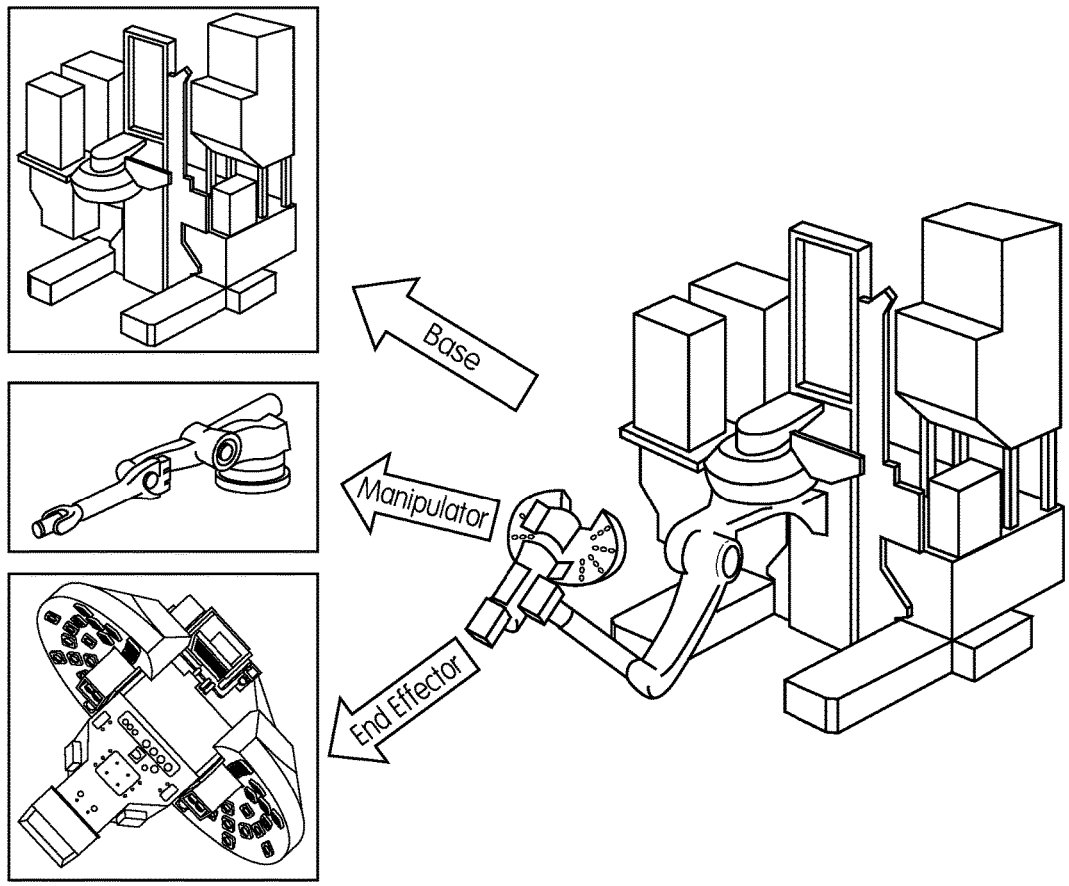
FIG. 28: Hierarchical robotic system composition model developed for this project: A whole "robot", on the right, is composed of a Base, a Manipulator, and an End Effector. The specific instance of each subcomponent, on the left, can be substituted for different, but analogous components, such as an alternate model of manipulator or alternate end effector geometry, without requiring any software alteration in the system.

The support software for this system also includes explicit software components and configuration metaphors for describing the constituent pieces of a robotic system, how they are assembled into whole robots, and how those robots interact with their environment to achieve some higher-level purpose. This so-called "Asset Model" allows the details of each individual robot, such as manipulator kinematics, calibrated end effector geometry, or mobile base capabilities to be expressed separately, and combined into a "robot" at a higher level, as shown in FIG. 28.

Expressing the constituency and composition of robotic systems in an explicit model in this manner higher-level software components, such as the various perception systems and planners described above, to control a variety of semantically similar, but heterogeneously detailed systems. It also allows for separate views of the system to be generated, such as for the GUI described above, but also to represent collision models, derive homogeneous transforms, etc., that guarantee a true representation of the system state without interfering with other system components.

Figure 29:
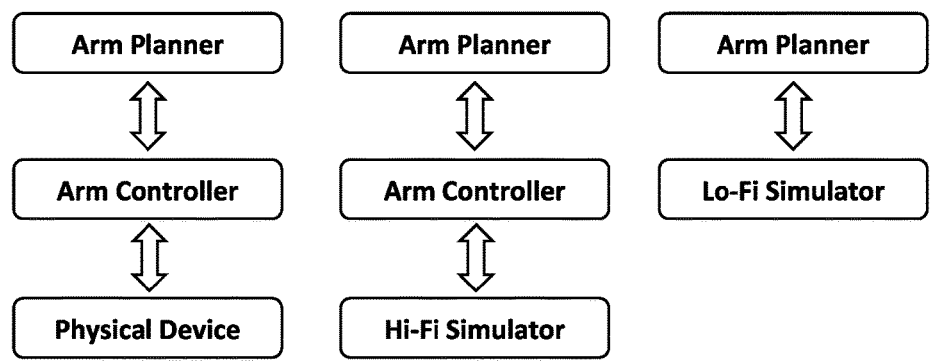
FIG. 29: Basic layering architecture, showing a model-controller-view separation of concerns for controlling and simulating an industrial manipulator (arm), in live (left), high-fidelity-simulated (center), and low-fidelity simulated (right) configurations.

The broad usage of this modeling paradigm, along with other appropriate applications of the Model-Controller-View design pattern, also allows the system to be completely simulated with varying degrees of fidelity. For example, as shown in FIG. 29, planning and control software be developed and tested offline by substituting the "real" arm control and interface processes with simulants of varying degrees of fidelity.

An important concept expressed in this diagram is that of behavioral variation by component substitution: none of the higher-level components need to "know" whether the lower-level components are real or simulated.

Similar simulation capabilities have been developed for all major subsystems of the robotic system presented in this paper, notably including the Mobile Base Unit, Mapping Sensor, and to a certain extent, the Global Localization system in addition to the Manipulator. This pervasive simulation capability allows all high-level planning software to be developed, tested and debugged offline. This, in turn, allows problems to be resolved or new features to be added to the system without consuming testing time on the real robot, reducing the risk of unexpected or erroneous behavior thereon. In one example, this simulation capability can be extended to be able to simulate the surface process as well. This can support experimentation with and optimization of system behaviors that arise from variations in the surface process, such as would arise from variations in paint thickness for laser coating removal.

We claim:

1. A method of performing surface processing on a three-dimensional object using a robotic manipulator having and end effector, with a stationary or mobile base, in a work environment comprising the steps of:

obtaining a base model of said three-dimensional object;

generating a surface model from said base model by performing a surface scan of said three-dimensional object and augmenting said base model with range data and surface property data obtained from said scan;

planning a temporal sequence of states of said robotic manipulator to maximize processing of said surface of said three-dimensional object while avoiding a collision between said three-dimensional object and other objects in said work environment;

placing said robotic manipulator in each state in said sequence of states, and, for each state:

scanning said surface of said three-dimensional object before said surface is processed to control or modulate a processing tool connected to said robotic manipulator;

processing said surface with said processing tool and;

scanning said surface of said three-dimensional object after said surface has been processed and updating said surface model with new surface property data;

adjusting said temporal sequence of states for said robotic manipulator based on said updated surface model;

measuring the three-dimensional position and orientation of said end effector relative to a work area on said surface using one or more relative position sensors to minimize pose error due to relative motion between work room positioning sensors and said robotic manipulator; and contintinuing processing of said surface and said updating of said surface model until said surface reaches a desired state.

2. The method of claim 1 further comprising the steps of:
refining the position of said surface model with respect to said work environment; and
refining the position of said robotic manipulator with respect to said work environment.

3. The method of claim 2 wherein said robotic manipulator is mounted on a mobile base which is capable of moving with respect to said work environment.

4. The method of claim 3 wherein said robotic manipulator is mounted on a rail base capable of moving said robotic manipulator along a rail.

5. The method of claim 1, wherein said base model is obtained from a pre-existing 3-D model with subsurface properties.

6. The method of claim 1, wherein said base model is generated by scanning said three dimensional object using an optical sensor capable of capturing the shape of said three dimensional object.

7. The method of claim 1 further comprising the step of augmenting said base model with processing policies regarding the processing of said surface.

8. The method of claim 7 further comprising the step of allowing user interaction with said surface model.

9. The method of claim 8 wherein said user interaction includes allowing the specification of masks which preclude portions of said surface from being processed.

10. The method of claim 8 wherein said user interaction includes allowing the specification of keep out areas or volumes which prevents the positioning of said robotic manipulator over said specified area or inside said specified volume.

11. The method of claim 8 wherein said user interaction includes allowing the marking of an area that needs further processing.

12. The method of claim 8 wherein said user interaction allows the overriding of said processing policies.

13. The method of claim 1 wherein said robotic manipulator includes a LIDAR device and further wherein said range data is generated by said LIDAR device.

14. The method of claim 1 wherein said robotic manipulator includes one or more sensors, and further wherein said surface property data is generated by said one or more sensors.

15. The method of claim 14 wherein said one or more sensors is selected from a group comprising multi-spectral cameras, color cameras, monochrome cameras and cameras with specific wavelength sensitivities.

16. The method of claim 14 wherein said one or more sensors is selected from a group comprising inspection sensors, including non-destructive inspection sensors, ultrasonic sensors, and eddy current based crack detection sensors.

17. The method of claim 1 wherein said temporal sequence of states of said robotic manipulator comprises a set of positions with respect to said work environment and poses.

18. The method of claim 1 wherein said step of planning a temporal sequence of states of said robotic manipulator precludes processing the same area of said surface more than once within a predetermined minimum period of time.

19. The method of claim 1 wherein said surface model consists of a set of two dimensional manifolds, each of said manifolds composed of a plurality of cells, each of said cells representing a physical unit of surface area and each of said cells having a set of properties associated therewith.

20. The method of claim 19 where said properties associated with each of said cells includes the type of material and coating properties.

21. The method of claim 1 wherein said processing tool is a laser capable of ablating paint from said surface.

22. The method of claim 1 further comprising the steps of:
querying the most recently observed state of said surface along a trajectory of said processing tool; and
planning a sequence of processing actions and parameters to be carried out by said processing tool based on said observed state.

23. The method of claim 1 further comprising the step of analyzing a processed surface to determine if further processing is necessary for any portion of said surface.

24. The method of claim 1 wherein said robotic manipulator includes an end effector, further comprising the step of measuring the 3-D position and orientation of said end effector using an optical positioning camera sighting said surface to measure relative motion between said end effector and said surface as said processing tool is processing said surface.

25. A system for performing surface processing on a three-dimensional object in a work environment comprising:
one or more robotic manipulators, each of said robotic manipulators including an end effector having a surface processing tool, a ranging sensor and one or more surface property sensors attached thereto, said one or more robotic manipulators being mounted on a stationary base or mobile base capable of moving on a surface;
a computer running software for controlling said one or more robotic manipulators, said software comprising:
a surface property analyzer, for processing surface properties sensor data before and after the processing point of said surface processing tool to classify the current state of said surface;
a surface model for storage of the geometry of said surface and said current state of said surface, wherein the software is adapted to generate the surface model by refining a three-dimensional base model by the surface property analyzer performing a surface scan of said three-dimensional object and augmenting said base model with range data and surface property data obtained from said scan;
a surface process planner for planning a sequence of processing actions to be carried out by said processing tool based on an observed state of said surface stored in said surface model, wherein the surface process planner is adapted to create a temporal sequence of states of said one or more robotic manipulators comprising a set of positions and poses to maximize processing of said surface of said three-dimensional object while avoiding a collision between said three-dimensional object and said robotic manipulators;

a surface process modulator for modifying said planned sequence of processing actions based on real-time feedback from said ranging sensor and said one or more surface property sensors; and a surface coverage planner, for planning movements and poses of said one or more robotic manipulators to maximize coverage of said surface;

wherein said one or more robotic manipulators each includes one or more relative position sensors for measuring the three-dimensional position and orientation of the end effector for each of said robotic manipulators relative to a work area to minimize pose error due to relative motion between optical based positioning and each of said robotic manipulators.

26. The system of claim 25 wherein said processing tool is a laser capable of ablating paint from said surface.

27. The system of claim 25 further comprising one or more sensors for detecting and locating objects surrounding said system to prevent collision with said objects.

28. The system of claim 25 wherein said one or more robotic manipulators are mounted on a rail base capable of moving said one or more robotic manipulators along a rail.

29. The system of claim 25 wherein said ranging sensor is selected from a group comprising a scanning laser rangefinder, a stereo camera, a range camera and a range capture sensor.

30. The system of claim 25 wherein said one or more surface property sensors are selected from a group comprising video cameras and inspection sensors.

31. The system of claim 25 further comprising active illumination to illuminate the area viewed by said one or more surface property sensors.

32. The system of claim 25 wherein said software allows manual editing of said surface model by a user to effect changes in said sequence of processing actions.

33. The system of claim 25 wherein said surface is the fuselage, wings and control surfaces of an aircraft and further wherein said surface processing is the removal of coating layers from said surface.

* * * * *